US006587581B1

(12) United States Patent
Matsuyama et al.

(10) Patent No.: US 6,587,581 B1
(45) Date of Patent: *Jul. 1, 2003

(54) VISUAL INSPECTION METHOD AND APPARATUS THEREFOR

(75) Inventors: Yukio Matsuyama, Nasu-machi (JP); Yuji Takagi, Yokohama (JP); Takashi Hiroi, Yokohama (JP); Maki Tanaka, Yokohama (JP); Asahiro Kuni, Naka-machi (JP); Junzou Azuma, Ebina (JP); Shunji Maeda, Yokohama (JP); Chie Shishido, Yokohama (JP)

(73) Assignee: Hitachi, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/006,371

(22) Filed: Jan. 12, 1998

(30) Foreign Application Priority Data

Jan. 10, 1997  (JP) .............................................. 9-002667

(51) Int. Cl.⁷ ................................................. G06K 9/00
(52) U.S. Cl. ....................... 382/149; 382/169; 382/219; 382/274; 250/305; 250/397
(58) Field of Search ............................... 382/108, 149, 382/151, 168, 169, 181, 171, 172, 170, 173, 199, 274, 287, 289, 219; 356/237.2; 250/559.42, 310, 307, 392, 305

(56) References Cited

U.S. PATENT DOCUMENTS

| | | | | |
|---|---|---|---|---|
| 3,903,363 A | * | 9/1975 | Montone et al. ............... 348/87 |
| 4,443,096 A | * | 4/1984 | Johannsmeier et al. ........ 355/43 |
| 4,532,650 A | * | 7/1985 | Wihl et al. .................. 348/126 |
| 4,579,455 A | * | 4/1986 | Levy et al. .................. 356/394 |
| 4,614,430 A | * | 9/1986 | Hara et al. .................. 382/149 |
| 4,805,123 A | * | 2/1989 | Specht et al. ................ 382/144 |
| 4,878,114 A | * | 10/1989 | Huynh et al. ............... 382/108 |
| 4,975,970 A | * | 12/1990 | Zettel et al. ................ 382/131 |
| 4,985,930 A | * | 1/1991 | Takeca et al. ............... 382/306 |
| 5,091,963 A | * | 2/1992 | Litt et al. .................... 358/101 |
| 5,216,481 A | * | 6/1993 | Minato ..................... 250/223 B |
| 5,412,210 A | * | 5/1995 | Todokoro et al. ........... 250/310 |
| 5,502,306 A | * | 3/1996 | Meisburger et al. ........ 250/310 |
| 5,568,563 A | * | 10/1996 | Tanaka et al. ............... 382/149 |
| 5,621,813 A | * | 4/1997 | Brown et al. ............... 382/151 |
| 5,724,456 A | * | 3/1998 | Boyack et al. .............. 382/274 |
| 5,727,080 A | * | 3/1998 | Cox et al. ................... 382/168 |
| 5,808,735 A | * | 9/1998 | Lee et al. .............. 250/559.42 |
| 5,830,612 A | * | 11/1998 | Yamada et al. ................. 430/5 |
| 5,872,871 A | * | 2/1999 | Yokoyama et al. ......... 382/173 |
| 5,943,437 A | * | 8/1999 | Sumie et al. ............... 382/149 |
| 6,172,363 B1 | * | 1/2001 | Shinada et al. ............. 250/310 |

\* cited by examiner

*Primary Examiner*—Timothy M. Johnson
*Assistant Examiner*—Sheela Chawan
(74) *Attorney, Agent, or Firm*—Antonelli, Terry, Stout & Kraus, LLP

(57) ABSTRACT

The present invention provides a scanning electron microscope (SEM) or optical inspection method and apparatus which correct differences in brightness between comparison images and thus which is capable of detecting a fine defect with a high degree of reliability without causing any false defect detection. According to the present invention, the brightness values of a pattern, which should be essentially the same, contained in two detected images to be compared are corrected in such a manner that, even if there may be a brightness difference in a portion free from defects, the brightness difference is reduced to such a degree so that it can be recognized as a normal portion. Also, a limit for the amount of correction is furnished in advance, and correction exceeding such limit value is not performed. Such correction prevents the difference in brightness that should be permitted as non-defective from being falsely recognized as a defect without overlooking great differences in brightness due to a defect.

59 Claims, 18 Drawing Sheets

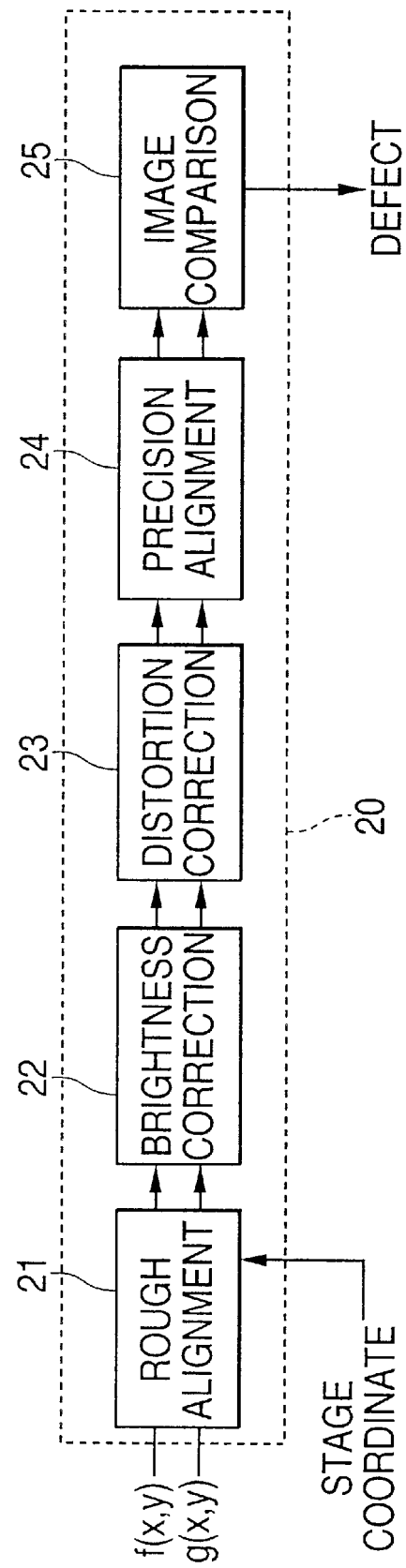

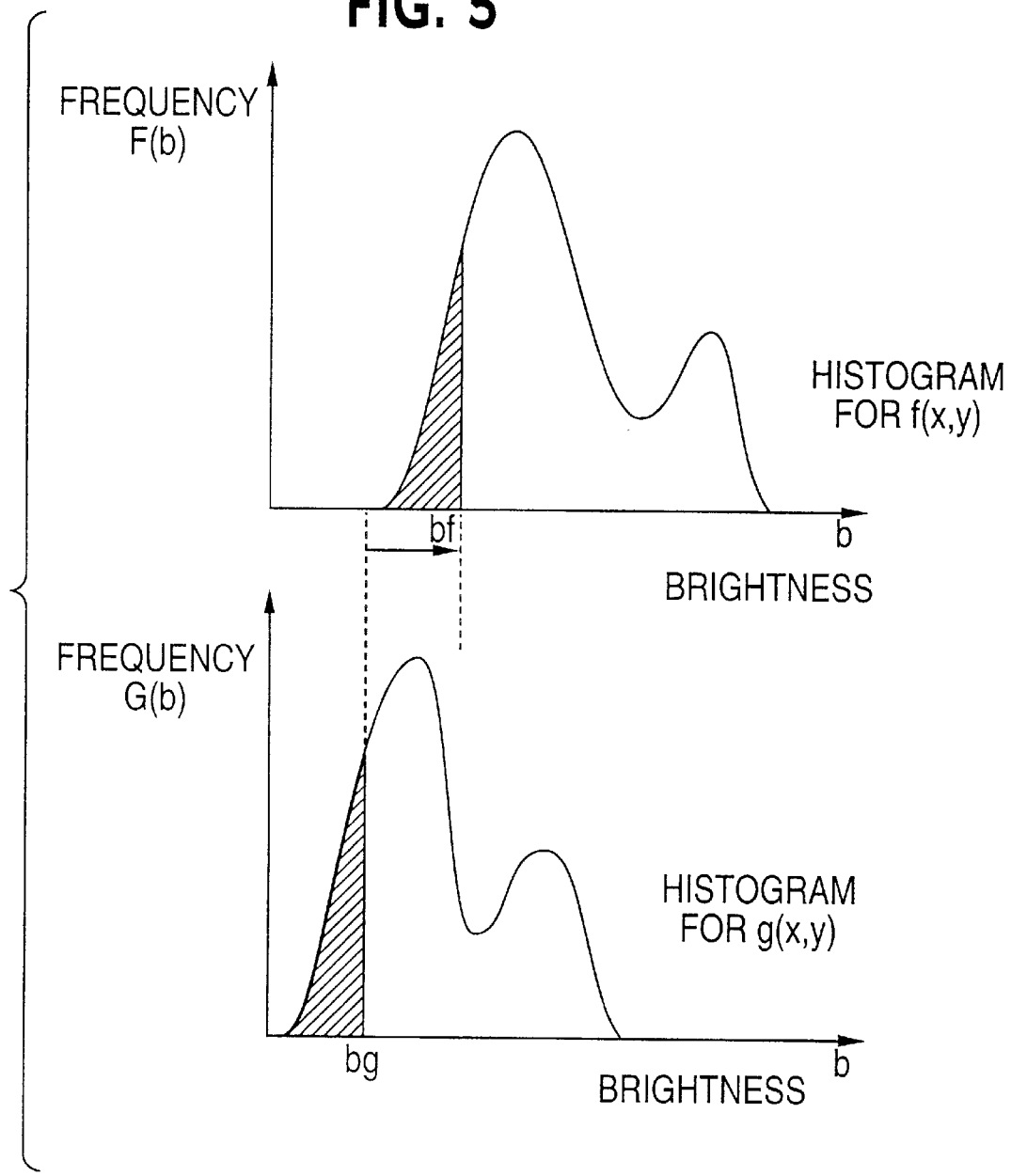

FIG. 8a
FIG. 8b
FIRST STAGE
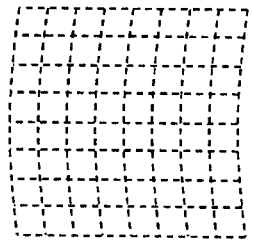
LARGE DIVISION UNIT
SECOND STAGE
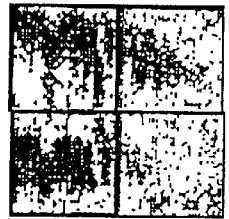
MIDDLE DIVISION UNIT
THIRD STAGE
SMALL DIVISION UNIT

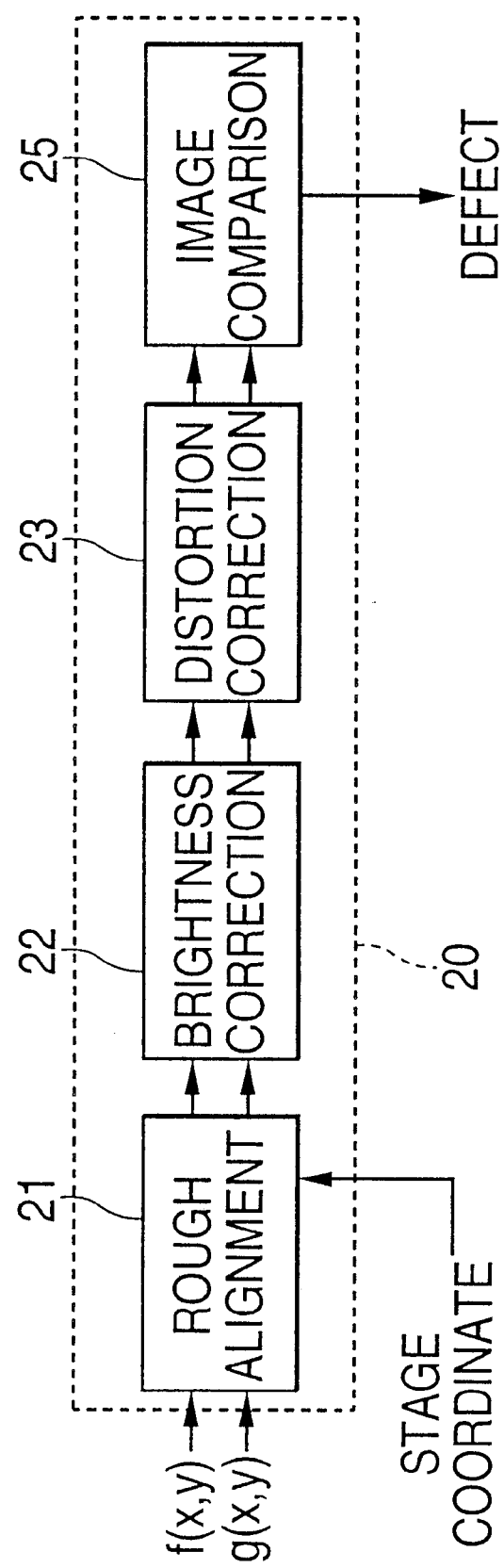

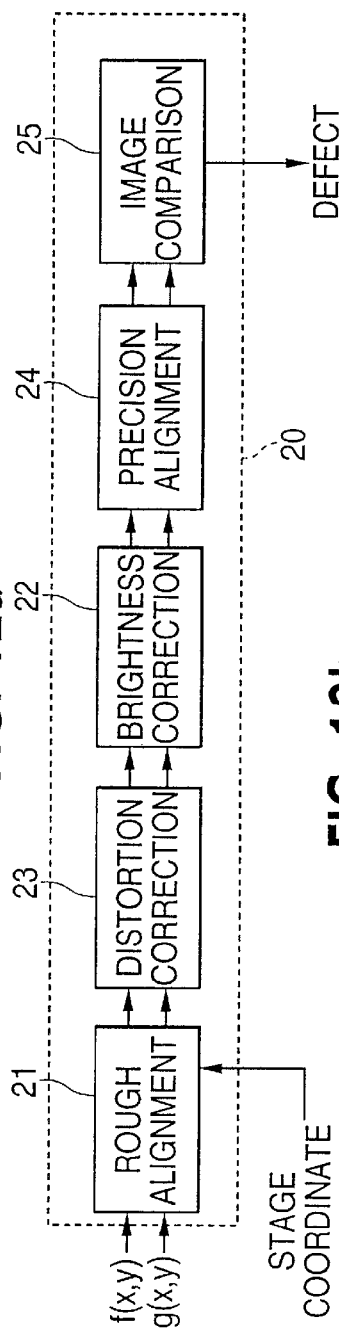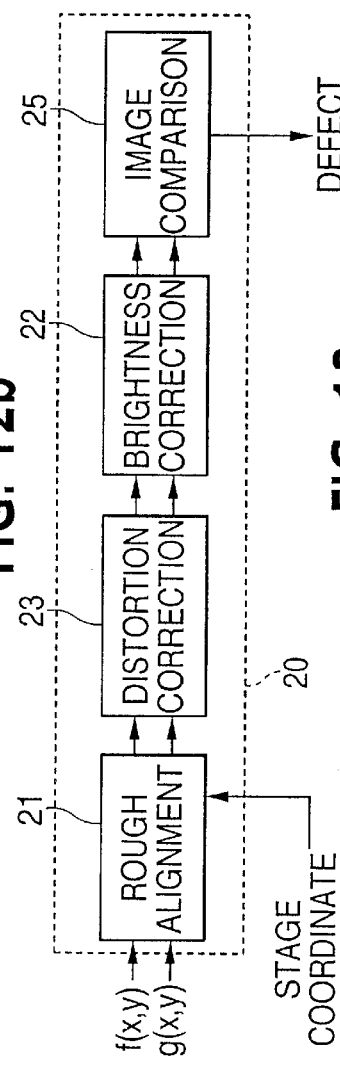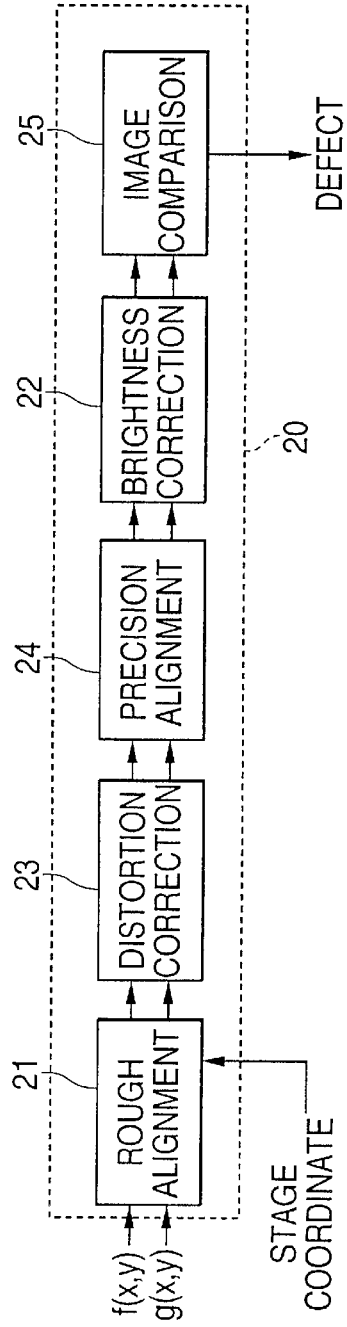

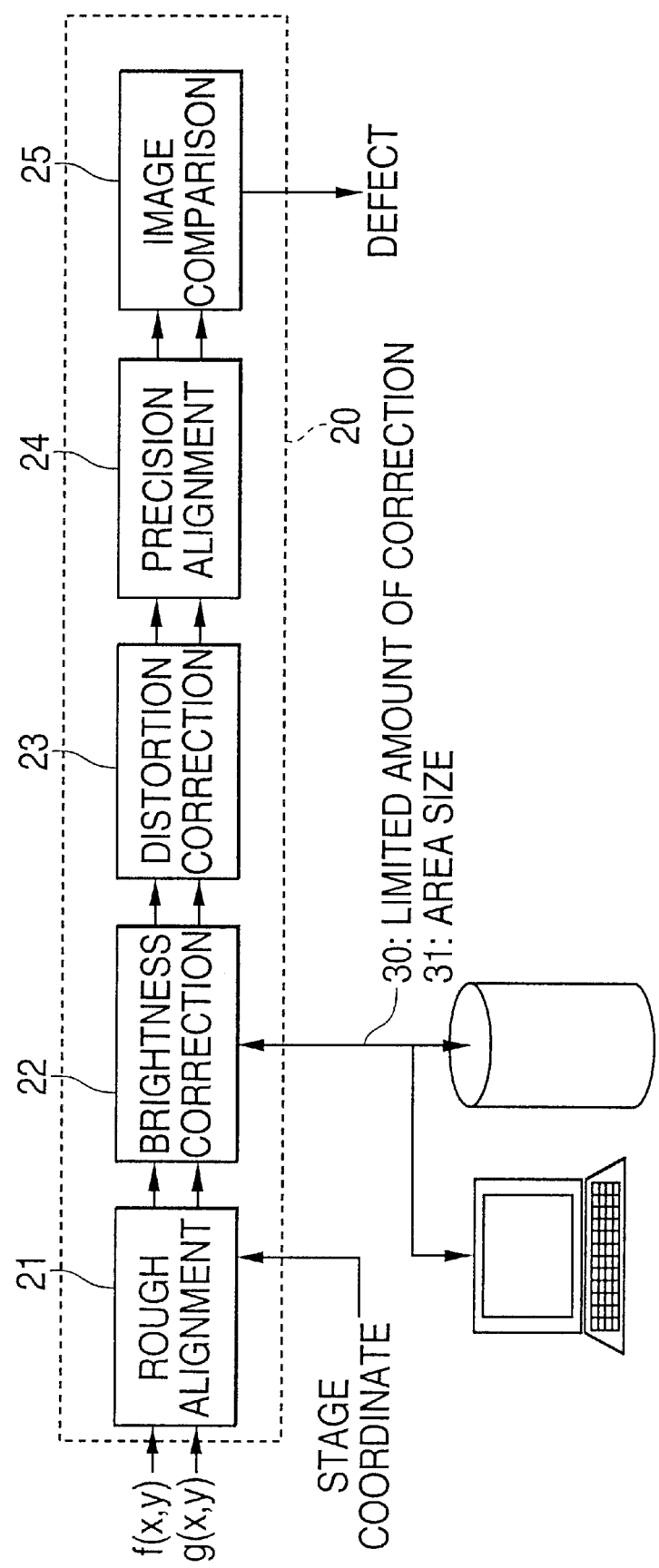

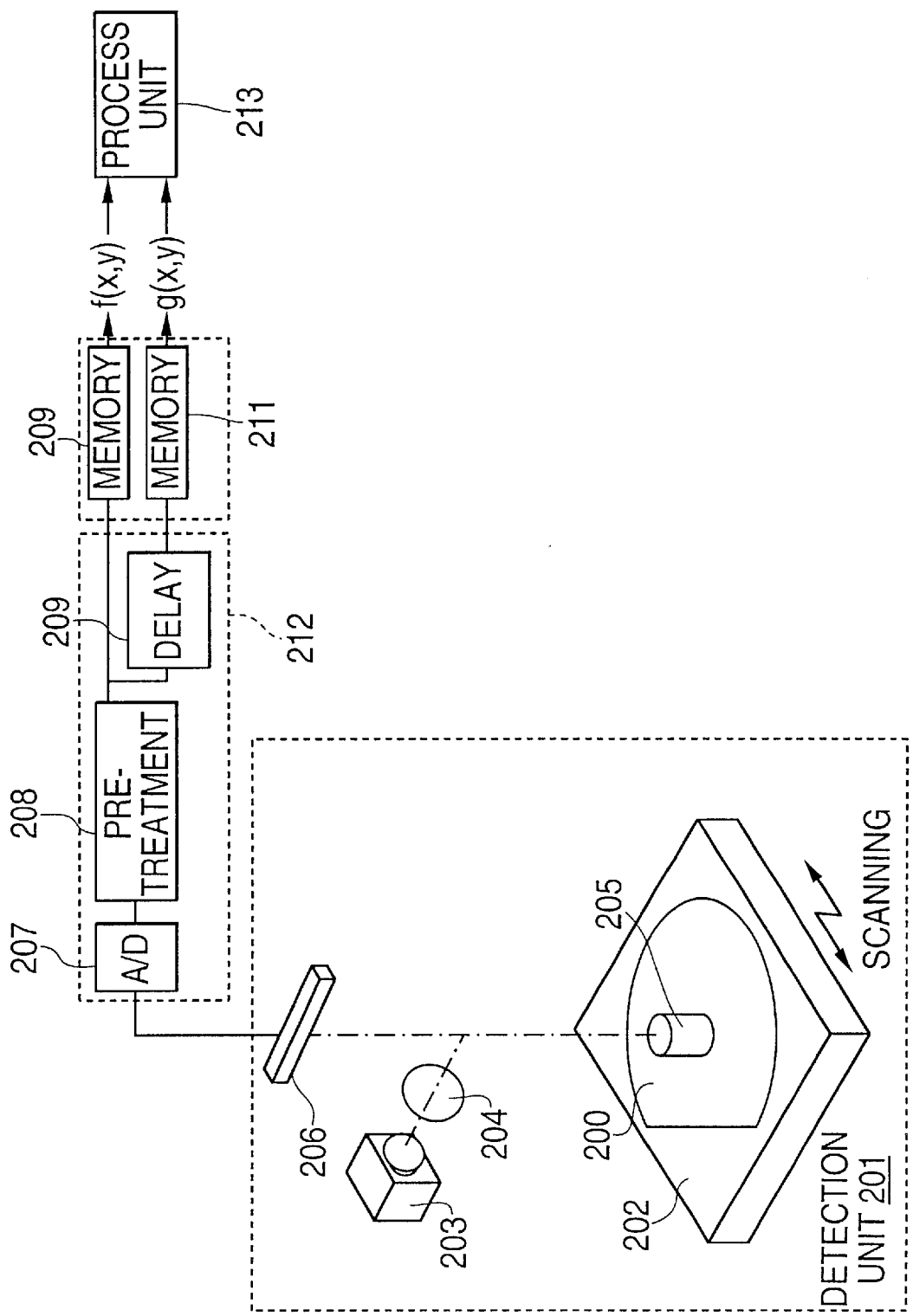

VISUAL INSPECTION METHOD AND APPARATUS THEREFOR

BACKGROUND OF THE INVENTION

1. Field of the Invention

The present invention relates to a method and apparatus which obtains two-dimensional images of an object (using an electron beam or optical arrangement), removes brightness level differences or distortions between the images via correction or equalization, and compares the resultant images so as to more accurately detect any defect contained in the object, for example, defects within a fine pattern of semiconductor wafers.

2. Description of Related Art

As a background visual inspection method for semiconductor wafers, there has been used a method for picking up, by use of optical means, two-dimensional images of different wafer areas or chips having corresponding patterns thereon (which should be essentially the same), and then to compare two detected images to determine differences therebetween as defects. More particularly, a simple differential image between the images is obtained, and any portion having a large differential value is regarded as a defect.

As a differing method not based on a simple differential image, there is a method described in, for example, "Automated Visual Inspection Of LSI Wafer Patterns Using A Derivative-Polarity Comparison Algorithm", SPIE Vol. 1567 Applications of Digital Image Processing XIV, pp. 100–109 (1991). According to this method, two optically detected brightness images to be compared are differentiated respectively, then only the polarities (in which direction the brightness gradient faces) of the differential value are extracted, and by comparing these polarities, any difference in brightness which occurs in the normal portions of two images makes it possible to detect fine defects in shape.

Also, as another comparison method, there is described "Precision Visual Inspection of LSI Wafer Pattern Using Local Perturbation Pattern Matching Method", i.e., in the thesis journal of Electronic Information Communications Association, Vol. J72-D-2, No. 12, pp. 2041–2050 (1989). This method is arranged to permit misregistration of not more than 1 pixel between two images optically detected, and also to permit any difference in brightness up to a certain specified level, and thus such method makes it possible to detect fine defects in shape without falsely detecting any difference in brightness occurring in a normal portion.

When defects in patterns in a fabrication process for semiconductor wafers having fine structure are inspected using an optical inspection method of the aforesaid background art, there were problems in that, for example, any non-opening defect of fine conducting holes, linear etching remainder (the width of whose short side is below the resolution of the optical system), and the like, cannot be detected because of the finely made wiring pattern formed on the semiconductor wafer. On the other hand, according to the inspection method using electron beams, it is possible to inspect defects in circuit patterns in the fabrication process of semiconductor wafers having the aforesaid fine structure.

When, however, for example, electron beams are irradiated to detect circuit patterns using secondary electrons from the object, the emission efficiency of the secondary electrons is determined by not only the material of the object, but also its film thickness, the acceleration voltage of the electron beams, the potential distribution in the vicinity of the object, and the like, and therefore, portions of the same material are not always detected at the same brightness. There are also some cases where a great difference in film thickness (which would cause no problems in the operation of the element) is erroneously determined defective as a result of a detected great brightness difference. There are also some cases where charge (so-called charge-up) accumulated in one area during detection forms a potential distribution which affects detection results of another area in its vicinity, and which results in brightness levels in the second area which are distorted.

When an image of the object is thus detected using electron beams, there was a problem that a pattern that is expected to be essentially detected at the same brightness is detected at a greatly differing brightness, and the difference in brightness is subsequently (i.e., erroneously) detected as a defect using the above brightness comparison inspection system. Also, according to the comparison system using the aforesaid differential polarity of the brightness image, a good result can be obtained for an image having little noise. However, if an image has high noise (e.g., in a system detecting images at high speed using electron beams), it is difficult to apply a differential equation as the same is prone to be affected by noise. Further, a method using a local perturbation pattern matching permits differences in brightness between images up to a certain specified level unconditionally, but if such differences in brightness violate the specified level, it becomes impossible to accurately detect only actual defects without detecting false detects.

As a further problem in the art, when electron beams are irradiated to detect circuit patterns using secondary electrons from the object, it was previously described that the electron beams are affected by the electrical conductivity of the inspection object. This not only causes the brightness of the detected image to become different, but also affects the irradiation position of the electron beams by influences of an electromagnetic field effect, and any misregistered positioning appears as a distortion in the detected image. Further, since this electrical conductivity depends upon the material of the object, the amount of misregistration due to this electrical conductivity distortion depends upon the electrical conductivity, the distribution of the material, and the thickness of the material, and further, the aforesaid amount of misregistration is not constant, but varies unsteadily.

As still a further problem, since a stage with an object specimen mounted thereon travels in vacuum in the electron beam method, and because there is a limit in how much mechanical friction can be reduced, vibration caused by friction of the stage during traveling also causes distortion in the detected image. The amount of slippage due to the above causes can be greater than a delicate fluctuation of the wiring pattern due to processing, and therefore, it is difficult to directly use the comparison system using differential polarity and the method based on the local perturbation pattern matching.

In the foregoing, description has been made of the case where electron beams are irradiated to detect circuit patterns using secondary electron from the object, and similar problems also occur in an optical inspection method because of the introduction of the fabrication process of CMP (Chemical Mechanical Polishing) and larger-sized wafer. CMP requires, in the fabrication process of semiconductors, polishing of each lamination layer to flatten the upper surface thereof, so as to prevent irregularity and waviness in the wiring structure for realizing a high level wiring structure. Since the layer on the top face has been flattened by polishing at the time of the inspection, a thickness of the layer (e.g., silicon dioxide) differs at differing surface positions. As a result, during optical inspection through the layer, an interference condition differs with position when viewed optically, diversified color is presented on an optically-observed image, resulting in varied brightness when detected on the monochromic brightness image.

As a further future difficulty, uniform formation of a wiring pattern over an entire wafer surface becomes more and more difficult as wafers continue tending toward larger-sized wafers. In the case of comparison inspection, it is conceived that the farther respective comparison patterns become separated, the greater a difference in pattern becomes. Thus, it is difficult to directly use the comparison system using differential polarity presupposing the delicate fluctuation and the method based on the local perturbation pattern matching.

A listing of further references directed to inspection approaches includes U.S. Pat. No. 5,502,306 issued to Meisburger et al., U.S. Pat. No. 5,649,022 issued to Maeda et al., U.S. Pat. No. 5,153,444 issued to Maeda et al., and U.S. Pat. No. 4,805,123 issued to Specht et al. The teachings of all U.S. Patents listed throughout this disclosure are herein incorporated by reference.

SUMMARY OF THE INVENTION

It is an object of the present invention to correct unsteady misregistration existent between two images to be compared, and to provide a visual inspection method and apparatus capable of detecting fine defects with a high degree of reliability without causing any false detection by correcting differences in brightness levels which occur in portions which should be recognized as normal portions.

In order to solve the aforesaid problem, according to the present invention the brightness values of a pattern which should be essentially the same in two detected images to be compared are corrected in such a manner that, even if there may be a brightness difference in a portion free from defects, the brightness difference in question is reduced to such a degree that it can be recognized to be a normal portion. In particular, the brightness correction is characterized by correcting so that the brightness of each area corresponding to the detected images to be compared become substantially the same, i.e., the brightness levels of the two images are equalized. Also, the brightness correction is characterized in that a limit for the amount of correction is furnished in advance and correction is performed not to exceed the limit value. Such correction prevents the difference in brightness of detected images due to a difference in film thickness of such a degree that should be permitted as non-defective from being falsely recognized as a defect. Also, it is possible to avert a danger of overlooking a great difference in brightness due to etching remainder or the like thinly existing at the bottom of a fine hole because of the brightness correction.

As a concrete brightness correction method, there are methods for performing the brightness correction: by linearly transforming the brightness value of one image; by determining the coefficient of linear transformation so that the sum of square of the difference between the one image and the other image for each pixel is minimized; by calculating a plurality of peak positions from a histogram for the brightness value of one image; by changing the brightness value of the one image so that the peak positions coincide with peak positions of a histogram for the brightness value of the other image calculated in the same manner; by changing the brightness value of the one image so that the histogram for brightness value of one image coincides with the histogram for brightness value of the other image in shape; etc. This listing of possible methods is, however, non-exhaustive.

The foregoing and other objects, advantages, manner of operation, novel features and a better understanding of the present invention will become apparent from the following detailed description of the preferred embodiments and claims when read in connection with the accompanying drawings, all forming a part of the disclosure hereof this invention. While the foregoing and following written and illustrated disclosure focuses on disclosing embodiments of the invention which are considered. preferred embodiments, it should be clearly understood that the same is by way of illustration and example only and is not to be taken by way of limitation, the spirit and scope of the present invention being limited only by the terms of the appended claims.

BRIEF DESCRIPTION OF THE DRAWINGS

The following represents brief descriptions of the drawings, wherein:

FIG. 2 is a block diagram showing an image processing and defect determination unit according to the present invention;

FIG. 5 contains still further graphs explaining another operation brightness correction according to the present invention;

FIGS. 8a–b contains views schematically showing a state in which a distorted image is divided into smaller areas in a stepwise manner;

FIG. 11 is a block diagram showing an image processing and defect determination unit according to the present invention;

FIGS. 12a–c are block diagrams showing differing image processing and defect determination units according to the present invention;

FIG. 14 is a block diagram showing another embodiment of an image processing and defect determination unit of a visual inspection apparatus according to the present invention;

FIG. 15 is a schematic view showing an embodiment of an inspection apparatus according to the present invention;

DETAILED DESCRIPTION OF THE PREFERRED EMBODIMENTS OF THE INVENTION

Figure 1:
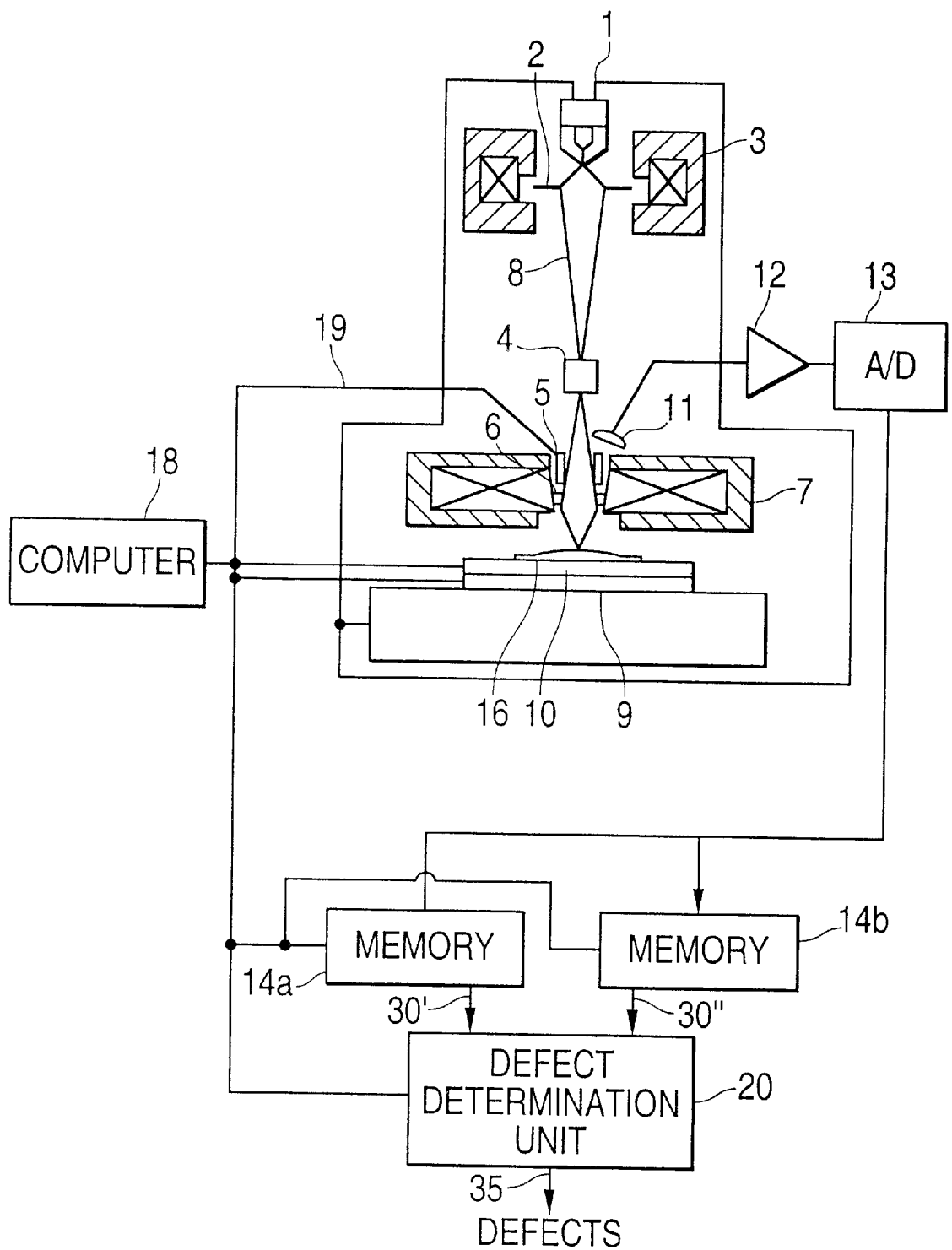
FIG. 1 is a schematic cross-sectional view showing an embodiment of an inspection apparatus according to the present invention.

Before beginning a detailed description of the subject invention, mention of the following is in order. More particularly, when appropriate, like reference numerals and characters are used to designate identical, corresponding or similar components in differing figure drawings.

Hereinafter, description will be made of embodiments according to the present invention by exemplifying an inspection apparatus using electron beams (i.e., a scanning electron microscope (SEM) arrangement) with reference to the drawings. FIG. 1 is a view schematically showing a defection system for electronically scanning a semiconductor wafer as an inspection object. The electronic optical system is composed of an electron gun 1, electron beams drawing electrodes 2, a condenser lens 3, a blanking deflector 4, a scanning deflector 5, a diaphragm 6, and an object lens 7. Reference numeral 8 designates an irradiated electrode beam. A sample chamber is composed of a X-Y stage 9 and a rotation stage 10. A secondary electron detector 11 is located above the object lens 7, and an output signal from the secondary electron detector is amplified by a pre-amplifier 12 to be converted into digital data by a A-D converter 13. The digital data is stored in image memories 14a and 14b to be inputted via lines 30', 30" to an image processing and defect determination unit 20, to be processed thereby, resulting in a defect output along line 35.

Reference numeral 16 designates a semiconductor wafer to be inspected, which has been loaded on the X-Y stage 9 and/or rotation stage 10. A computer 18 supplies control signals to appropriate components for control and/or coordination of the same via a bus 19, for example, a non-exhaustive list of such components includes scanning deflector 5, X-Y stage 9, rotation stage 10, image memories 14a and 14b, and defect determination unit 20.

During inspection, the X-Y stage 9 mounted with the semiconductor wafer inspected 16 thereon continuously moves at a constant speed in the X direction. During this period, the electron beam 8 is allowed to scan in a straight line in the Y direction by the scanning deflector 5. As alternative arrangements, scanning could be effected purely by the scanning deflector 5 arrangement. Also, the rotation stage 10 can also be utilized in a scanning operation. As a result of such versatile arrangement, electron beams can be irradiated onto any predetermined portion or the entire circuit pattern of the semiconductor wafer 16 to form an image suitable in size, resolution and shape for a desired inspection area.

While the electron beams 8 are irradiated onto the semiconductor wafer 16 being inspected, secondary electrons generated thereon are emitted and then received and detected as an electric signal by the detector 11. The electric signal detected is converted by the A-D converter 13 thereby to be digitized. Thus, information on image brightness is stored in the memory 14a or 14b as a brightness gradation value over time or location, and corresponding to a desired pixel size. By repeating this operation and keeping the correspondence between the electron beams irradiation position and the amount of detected secondary electron emission, a two-dimensional secondary electronic image for the semiconductor wafer 16 is stored. By transmitting the detected signal after digitizing, the image can be flexibly processed at high speed and at a high signal to noise ratio. Further, a fixed or variable delay circuit can be provided between the A-D converter 13 and either or both of the memories 14a and 14b to accommodate a proper timing in a handling of the image information.

The secondary electronic image formed and transmitted by the aforesaid method is stored in the plurality of memories 14a and 14b. When comparative inspection is performed between areas (or chips), a secondary electronic image for the inspection area A (or chip A) is first stored in the memory 14a. Next, a secondary electronic image of a corresponding inspection area B (or chip B) which is preferably adjacent to (but may be distant from) area A is stored in the memory 14b, and the corresponding stored images are compared in the defect determination unit 20. Note that comparison of the images is preferably conducted simultaneous with storage (i.e., for time efficiency), or alternatively (if time efficiency is not a concern), comparison can be made after storage has been completed. In an ongoing inspection, a secondary electronic image for the next area C (or chip C) is obtained and stored in the memory 14a, and is compared with the image for the area B (or chip B) in the memory 14b while being stored. This operation is repeated, until all the inspection areas or chips have been stored and compared to detect any different portions as defects.

In addition to this method, there can be also used a method for allowing a standardized secondary electronic image of an inspection area of the semiconductor wafer 16 to be stored in the memory 14a in advance, and for such standardized image to be used as a comparison template. After the inspection area and the like for a non-defective semiconductor wafer 16' is set on the inspection apparatus, inspection is performed to obtain a first secondary electronic image of a desired area and is stored in the memory 14a. Next, a (non-standardized) semiconductor wafer 16 for actual defect inspection is loaded on the inspection device, and is inspected using the same method. A second secondary electronic image is taken in the memory 14b, and alignment, various image processing and comparison are performed between the first secondary electronic image and the second secondary electronic image to thereby detect only the defects.

While the above embodiment is illustrated and described as containing two separate image memories 14a and 14b, such memories can instead be provided in a form of a single memory, e.g., single RAM or hard disk drive having separate memory areas thereof designated for storage of different images. Further, the image memories 14a and 14b can be in the form of a line memory, shift registers, etc., possibly operating in conjunction with a fixed or variable delay circuit to deliver appropriate image data to each respective memory or memory area.

Figure 16:
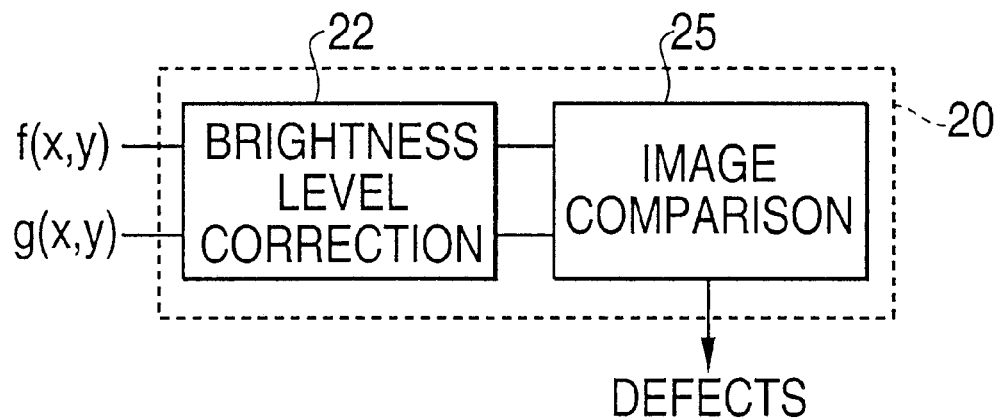
FIG. 16 is a block diagram showing a simplified image processing and defect determination unit according to the present invention.

FIG. 16 is a block diagram showing a simplified image processing and defect determination unit 20 according to an embodiment of the present invention. Images f(x, y) and g(x, y) from the image memories 14a and 14b are first inputted and are corrected by a brightness correction circuit 22 in such a manner that, even if there is a brightness level difference (e.g., because of scanning electron microscope (SEM) approach distortions due to SEM charge accumulation, or optical approach distortions due to optical layer thicknesses), the brightness difference in question is reduced by the brightness correction circuit 22 to such a degree that the image can be recognized as a normal image (i.e., without brightness level distortions). A comparative process is then performed by a brightness comparison circuit 25 to detect and output information regarding defects.

FIG. 2 is a block diagram showing a more sophisticated image processing and defect determination unit 20 according to an embodiment of the present invention.

Images f(x, y) and g(x, y) from the image memories 14a and 14b are first inputted into a rough alignment circuit 21 (which also receives stage coordinate information). After being roughly aligned within the rough alignment circuit 21, the brightness values contained in the two detected images having patterns to be compared should ideally b the same, but in practice, such brightness values are distorted for the reasons indicated above. Such brightness distortions are corrected (or equalized) by a brightness correction circuit 22 in such a manner that, even if there may be a brightness difference in a portion free from defects, the brightness difference in question is reduced to such a degree that it can be recognized to be a normal portion.

Next, in order to remove any influence due to unsteady image distortion, any misregistration within the brightness corrected images is corrected by a distortion correction circuit 23 in such a manner that the image distortion is not detected as a defect. Thereafter, the two images outputted from the distortion correction circuit 23 are aligned with a higher degree of accuracy by a precision alignment circuit 24. Thus, for the images having been subjected to processes of rough alignment, brightness correction, distortion correction and precision alignment, a comparative process is then performed by an image comparison circuit 25 to detect defects. Hereinafter, detailed description will be made of procedures carried out in each process block shown in FIG. 2.

First, the description will be made of the rough alignment process. The image detection system using electron beams is usually provided in a vacuum chamber, and therefore, a stage on which an inspection wafer is mounted is also provided under vacuum. This causes the running precision of the stage to become inferior to that in an atmosphere environment, and as a result, distortion of the stage coordinates will be caused between the images to be compared. Thus, the stage coordinate is stored in advance in synchronism with the detection of these two images, and the rough alignment circuit 21 receives the stage coordinate information and corrects any misregistration between the images due to the aforesaid distortion by use of this stage coordinate.

Figure 3A:
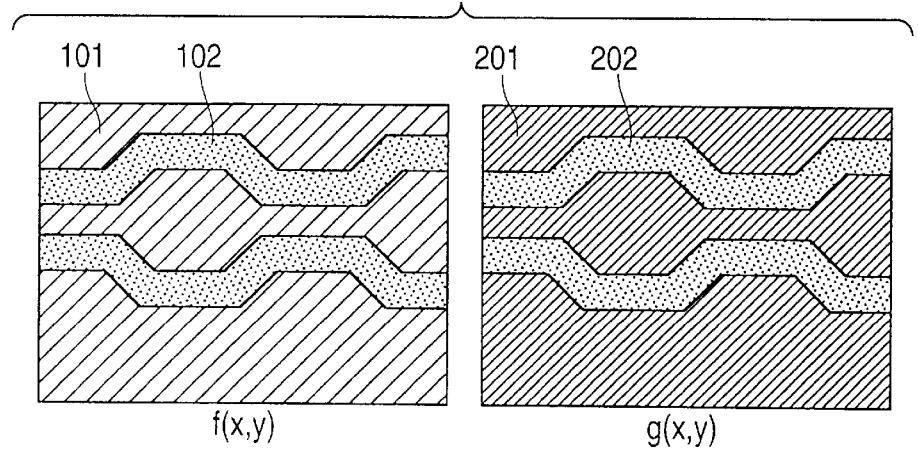
FIG. 3a contains plan views for a pattern for explaining difference in brightness levels for normal pattern portions, and FIG. 3b contains corresponding histogram graphs regarding the same.
Figure 3B:
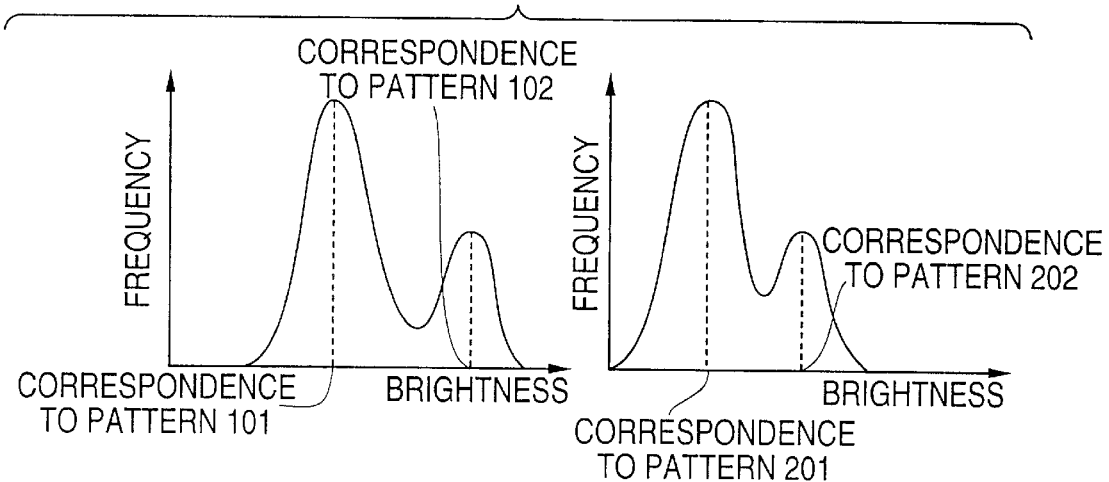

Next, detailed description will be made of a brightness correction operation. More particularly, FIG. 3a represents two brightness images f(x, y) and g(x, y) to be compared, and FIG. 3b represents histograms for the brightness values of the respective FIG. 3a images. Patterns 101 and 201, and patterns 102 and 202 are each formed of the same materials, respectively, and ideally should be detected essentially as having the same brightness level. However, as discussed previously, there are some cases where the brightness in the corresponding areas are detected with different brightnesses as shown in the figures, e.g., under the influence of slight differences in film thickness, and charge-up. More particularly, as can be clearly seen by a comparison of the FIG. 3b left-hand and right-hand histograms, the peak values of the two histogram plots are at differing brightness values and the range (or spread) between peaks within each histogram plot is different from the other histogram plot. In this case, the brightness level difference in these two images is not a small value, and as a result, even normal (i.e., non-defect) areas will be falsely recognized to be defective.

The simplest embodiment for brightness correction is based on a linear transformation method. More particularly, for one of the images to be compared, the coefficient of linear transformation can be determined by the least square method shown in the following equations:

$$e=\Sigma<|f(x, y)-\{a*g(x, y)+b\}|*|f(x, y)-\{a*g(x, y)+b\}|> \quad \text{(equation 1)}$$

$$\delta e/\delta a=0, \delta e/\delta b=0 \quad \text{(equation 2)}$$

where $\Sigma$ in equation 1 relates to x and y.

The coefficient of transformation is determined from equations 1 and 2 so that the sum of square of the difference between one image subjected to the linear transformation and the other image for each pixel is minimized. In this embodiment, when there are only two kinds of patterns contained in the images as shown in the example of FIG. 3, it is possible to allow the brightness of the corresponding areas to coincide with each other roughly, and to reduce the probability of falsely recognizing the normal portion to be defective by a differential operation. If three or more kinds of patterns are contained in an image and the brightness of their respective patterns are complicatedly different, and the brightness correction cannot be performed by simple linear transformation.

Figure 4A:
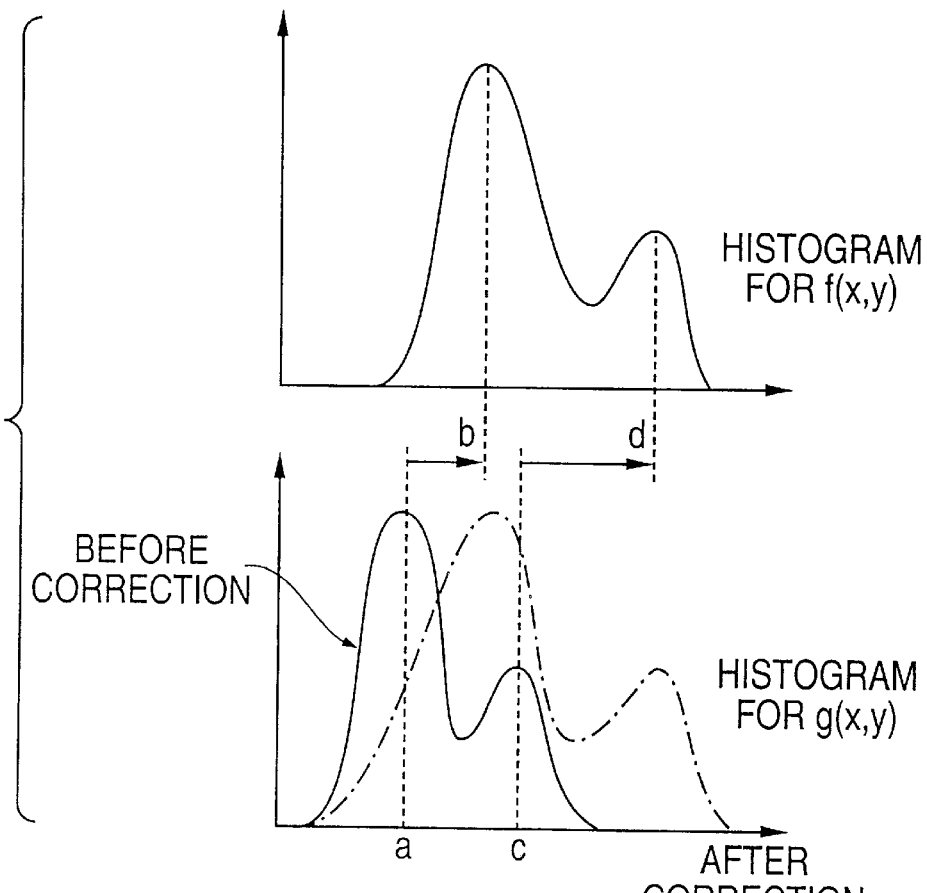
FIGS. 4a–b are further graphs explaining one operation for brightness correction according to the present invention.
Figure 4B:
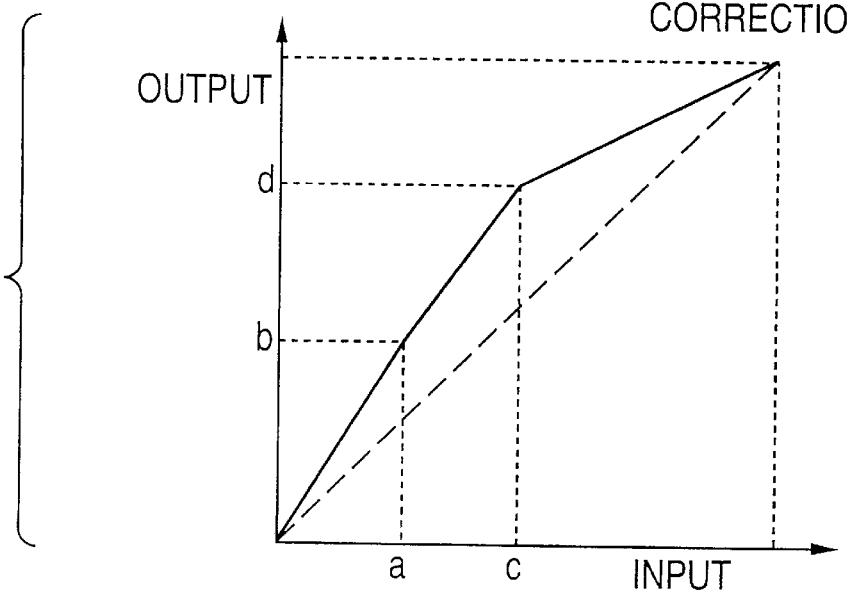

FIGS. 4a–b show a method for performing brightness conversion using the histogram of an image according to another brightness correction embodiment according to the present invention. FIG. 4a shows a case of two kinds of patterns in the same manner as shown in FIG. 3b, but this method can be applied to any case having three or more kinds of patterns similarly. More specifically, FIG. 4a contains an upper histogram for f(x, y), and a lower histogram for g(x, y). The two kinds of patterns contained in f(x, y) have peaks at brightnesses b and d respectively, and the peaks corresponding thereto within g(x, y) have brightnesses a and c respectively. Histogram conversion is performed for g(x, y) so that the two g (x, y) histogram peaks a and c coincide with the two f(x, y) histogram peaks b and d.

More specifically, the brightness conversion based on approximation of a polygonal line is performed as shown in FIG. 4b by converting the brightness within a range from origin O to a to that within a range from origin O to b, the brightness within a range from a to c to that within a range from b to d, and the range of brightness c and over to the range of brightness d and over. After such brightness correction, the histogram for g(x, y) and the histogram for f(x, y) coincide well with each other as indicated by an alternate long and short dash line in the FIG. 4a lower histogram, and the probability of falsely recognizing the normal portion to be defective becomes very low during the differential operation.

FIG. 5 shows another embodiment for the brightness correction according to the present invention. An area of the histogram G(b) for g(x, y) is integrated from a predetermined weaker brightness value to a certain value bg. Next, an area of the histogram F(b) for f(x, y) is integrated from a weaker brightness to a value bf similarly, with bf being determined so that the both integrated values bg and bf become equal. At this time, the pixel value for the brightness value bg contained in g(x, y) is converted into bf. While varying bg from O to the maximum value, the aforesaid brightness conversion is repeatedly performed to light-and-dark correct the entire image according to the following equation 3:

$$\sum_{b=0}^{bf} F(b) = \sum_{b=0}^{bg} G(b)$$

This conversion causes the histogram for g(x, y) and the histogram for f(x, y) to substantially coincide with each other after the brightness conversion, and the differential operation further reduces the probability of falsely recognizing the normal portion to be defective as compared with the aforesaid embodiment.

The aforesaid methods are all to convert brightness levels so that the brightness distribution of the one image is caused to coincide with that of the other image with each other. Also, if a number of predetermined (i.e., standardized) patterns or areas within the image are known in advance, it is possible to correct the brightness by preparing a model for the histogram on the basis of such predetermined patterns to match images with an appropriate model by the use of one of the aforesaid methods.

As described above, if the brightness correction is performed between images to be compared, any brightness distortion occurring in the normal portion will be corrected thereby to allow the arrangement to correctly detect only actual defects. As to defects involving not only difference in brightness but also difference in shape, it is possible to correctly detect defects having only less change in the brightness than the amount of correction. In the aforesaid method, however, it is conceivable that there may exist a case wherein a brightness difference based on a defect to be detected, is erroneously corrected together with brightness distortions, and thus the defect may be overlooked. More specifically, the following discussion concerns such situation.

Figure 6A:
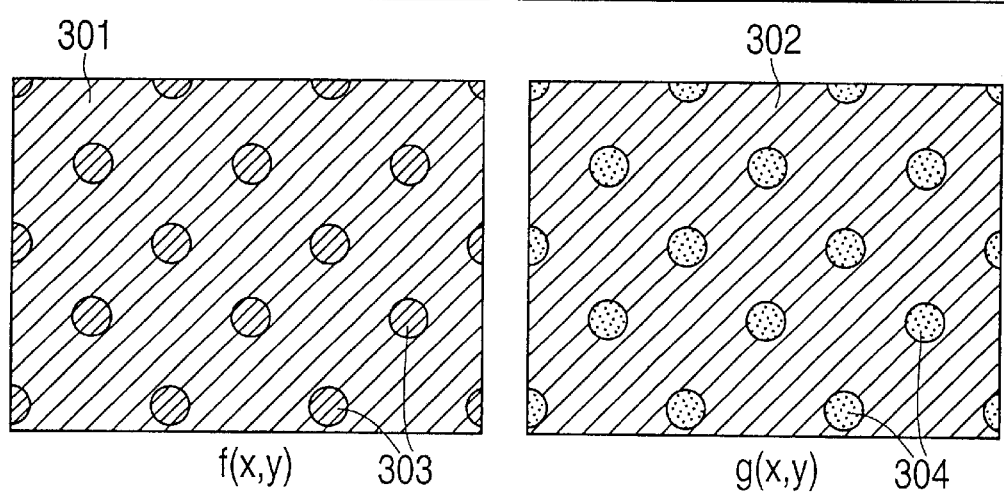
FIG. 6a contains plan views for a pattern for explaining difference in brightness levels in another pattern portion, and FIG. 6b contains corresponding histogram graphs regarding the same.
Figure 6B:
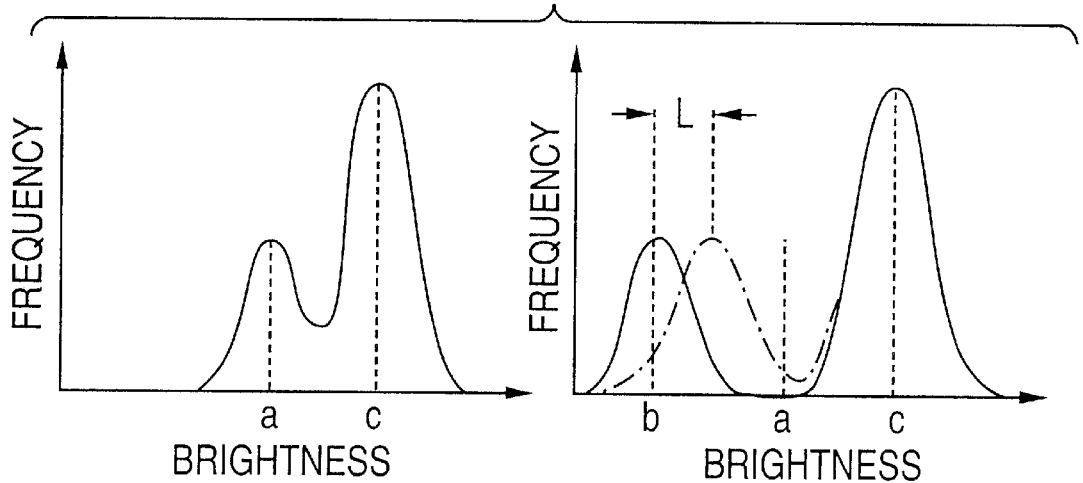

FIG. 6a shows (in a left-hand image) a normal pattern for fine holes, and (in a right-hand image) a defective pattern having residues such as resist at the bottoms of holes, and FIG. 6b shows their respective histograms. Patterns 301 and 302 (not having defects) are detected at the same brightness c, while pattern 303 is detected at brightness a, and pattern 304 (having the residue defects) is detected at brightness b. This difference in brightness is caused by the presence or absence of residues at the bottoms of the holes, and should be essentially detected as defects. If, however, the brightness a of the pattern 303 is excessively caused to coincide with the brightness b of the pattern 304 by the aforesaid brightness correction, this defect will be overlooked.

Thus, a predetermined limited amount L (FIG. 6b) for brightness correction is furnished in advance, and brightness correction is limited to such amount L such that correction of level differences which exceed beyond the limited amount are not performed. Accordingly, actual defects which typically have brightness differences which are much greater than brightness distortions (e.g., SEM approach distortions due to SEM charge accumulation, or optical approach distortions due to optical layer thicknesses) are not wholly removed in the brightness distortion correction process. Thereby, it is possible to correctly detect such a defect (such as etching residues thinly existing at the bottoms of fine holes) without overcorrecting, i.e., without performing excessive brightness level correction which would have erroneously eliminated defect information. More particularly, the solid-lined curve in the right-hand histogram of FIG. 6b shows a case where the difference in brightness exceeds the limited amount, whereas the alternate long-and-short-dashed-line curve is obtained by correcting g(x, y) with the limited amount L of correction. For this reason, the etching residues existing at the bottoms of the fine holes can be detected as a difference in brightness even after the limited brightness correction.

Turning now to other areas of discussion, in image detection using electron beams, a relative speed of electron beams to the object inspected causes eddy current in the object, and slight misregistration occurs in the detected image under the influence of an electric field caused by this eddy current. If the relative speed is constant, the amount of misregistration is also constant, and therefore, no distortion occurs in the image. If, however, the relative speed fluctuates under the influence of a running accuracy of the stage, the amount of misregistration also fluctuates, and this fluctuation is detected as the distorted image. On the other hand, in an optical inspection method, since it becomes more and more difficult to form a wiring pattern which is uniform over the entire surface of a wafer because of larger-sized wafer, it is conceivable that the difference between patterns to be compared varies owing to the difference in process conditions at different positions on the wafer. This means that the misregistration of the patterns to be compared varies depending upon the position, and as a result, unsteady distortion is observed between these two images. For these reasons, even if rough alignment is performed, fine distortions of the image that could not be aligned via the overall (i.e., whole image) precision alignment exists in the image. More particularly, localized misregistration results in axial warping distortion of the images, wherein the axial warping distortion can be a simple bending of one or more axes, or a complex bending/twisting of one or more of the axes (see, e.g., illustration of FIG. 7).

In order to eliminate this influence, a distortion correction circuit 23 performs alignment in finer areas (i.e., image sub-divisions) of such a degree that the distorted image does not pose any problem and misregistration is not detected as a defect. Hereinafter, description will be made of three methods concerning distortion correction process for correcting misregistration between two images which exists because of spatial distortion.

Figure 7:
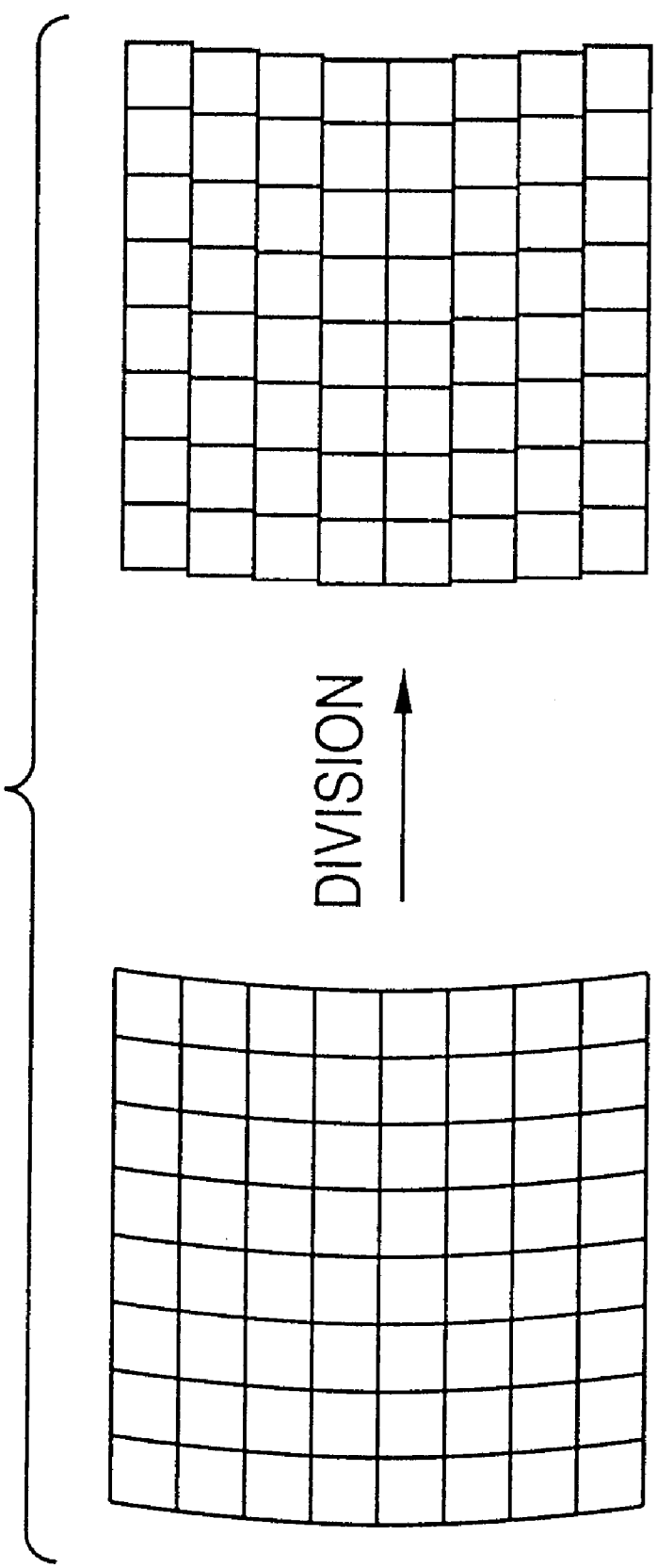
FIG. 7 contains views schematically showing a state in which a distorted image is divided into small areas and shifted for distortion correction.

First, a spatial distortion correction process using a division method will be described. If the detected image is distorted, a simplest method applicable is to divide the image as shown in FIG. 7 to such a small size and to compare corresponding divided units after alignment so as not to allow spatial distortion to pose any problem. At this time, if expected misregistration ranges are ±u in the x direction and ±v in the y direction, it is necessary to shift a divided unit in an amount up to ±u in the x direction and up to ±v in the y direction in order to perform alignment between corresponding divided units from the two respective images.

As another method, there is also conceivable a method for performing alignment in a stepwise manner by first performing larger sub-division rough (or coarse) alignment followed by one or more stages of smaller sub-division finer alignment. More particularly, the image is first divided roughly for rough alignment instead of immediately dividing it to minimum size units, and if further finer alignment is necessary, the image is further divided into smaller units for more precision alignment. FIGS. 8a–b show a state in which alignment is first performed at a larger sub-division unit (large division unit) having an area sixteen times as large as the minimum division unit. Thereafter, if necessary, alignment is performed at a medium sub-division unit (middle division unit) obtained by dividing each larger sub-division unit into four parts, and finally the medium sub-division unit it is further divided into four parts (small division unit) for small unit alignment. In the case of the stepwise division method, since rough alignment is performed in the previous stage, the lookup range for alignment at each stage requires a smaller area. On the other hand, in the case of the method for dividing to the minimum size from the beginning shown previously, since the lookup range inevitably becomes large, alignment may be performed to a pattern deviated by one pitch if the pattern pitch of the object is smaller than the lookup range. In other words, the stepwise alignment more easily enables correct alignment.

A third distortion correction process using a propagation method will be described. In the previously described methods, alignment is independently performed in each division unit respectively. As an alternative, it is also possible to perform alignment for a subject division unit by referring to an amount of misregistration for a neighboring division unit in its vicinity. More particularly, since the distorted image is continuous, it is impossible to have an amount of misregistration quite different from an amount of misregistration of the surrounding division unit. Therefore, if an amount of misregistration is determined at a specified division unit at the beginning, the amount of misregistration at a neighboring division unit will be able to be easily determined by utilizing the previous misregistration amount as a starting value when determining the misregistration amount of a new subject division unit. Thus the knowledge of previous neighboring misregistration amounts is allowed to propagate through processing of subsequent division units of the image, thereby accelerating a processing time and allowing scales of necessary circuitry and/or processing to be minimized.

Figure 9:
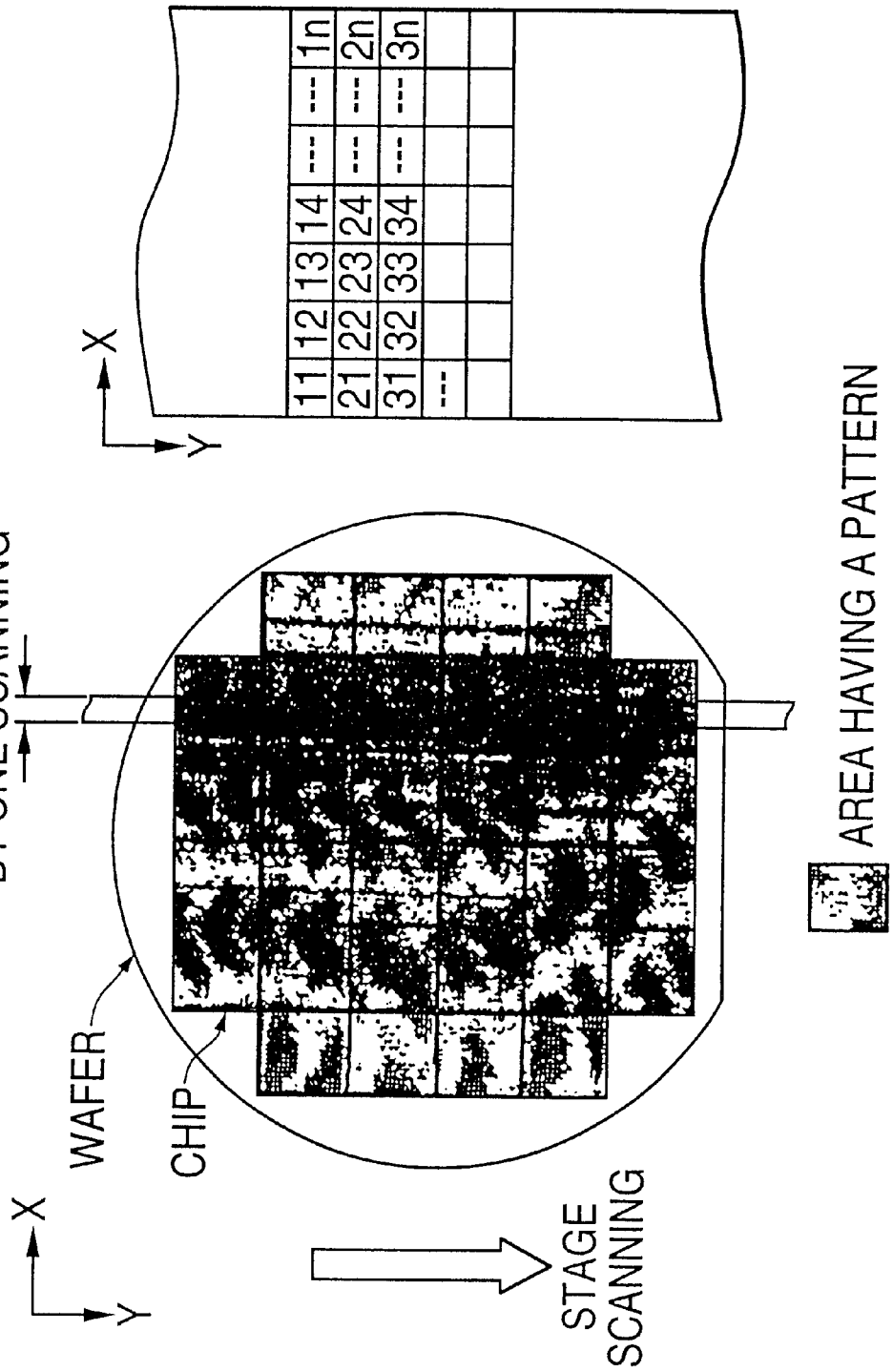
FIG. 9 is a view schematically showing a state in which an image with a fixed width is continuously inputted.

FIG. 9 shows a case where an image with a fixed width is continuously inputted by scanning of the stage. Division units 11 through 1n, 21 through 2n and 31 through 3n, etc., correspond to the division units in FIG. 7. Further, in the present example, units 11 through 1n are assumed to be a detected image for an edge portion of an area having a pattern, and if the amount of misregistration for the units 11 through 1n is determined at the beginning, the amount of misregistration for the units 21 through 2n can be easily determined by looking up within a small range on the basis of the amount of misregistration for units 11 through 1n. Subsequently, the amount of misregistration for units 31 through 3n is determined by looking up on the basis of the amount of misregistration for the units 21 through 2n. According to this method, since it will suffice if lookup for a large range is performed only at the beginning of each scanning, it becomes possible to reduce the hardware scale of a misregistration detection unit if, for example, the first lookup is performed with software and data to be inputted one after another during the period of time are arranged to be delayed by the software operation time.

Figure 10:
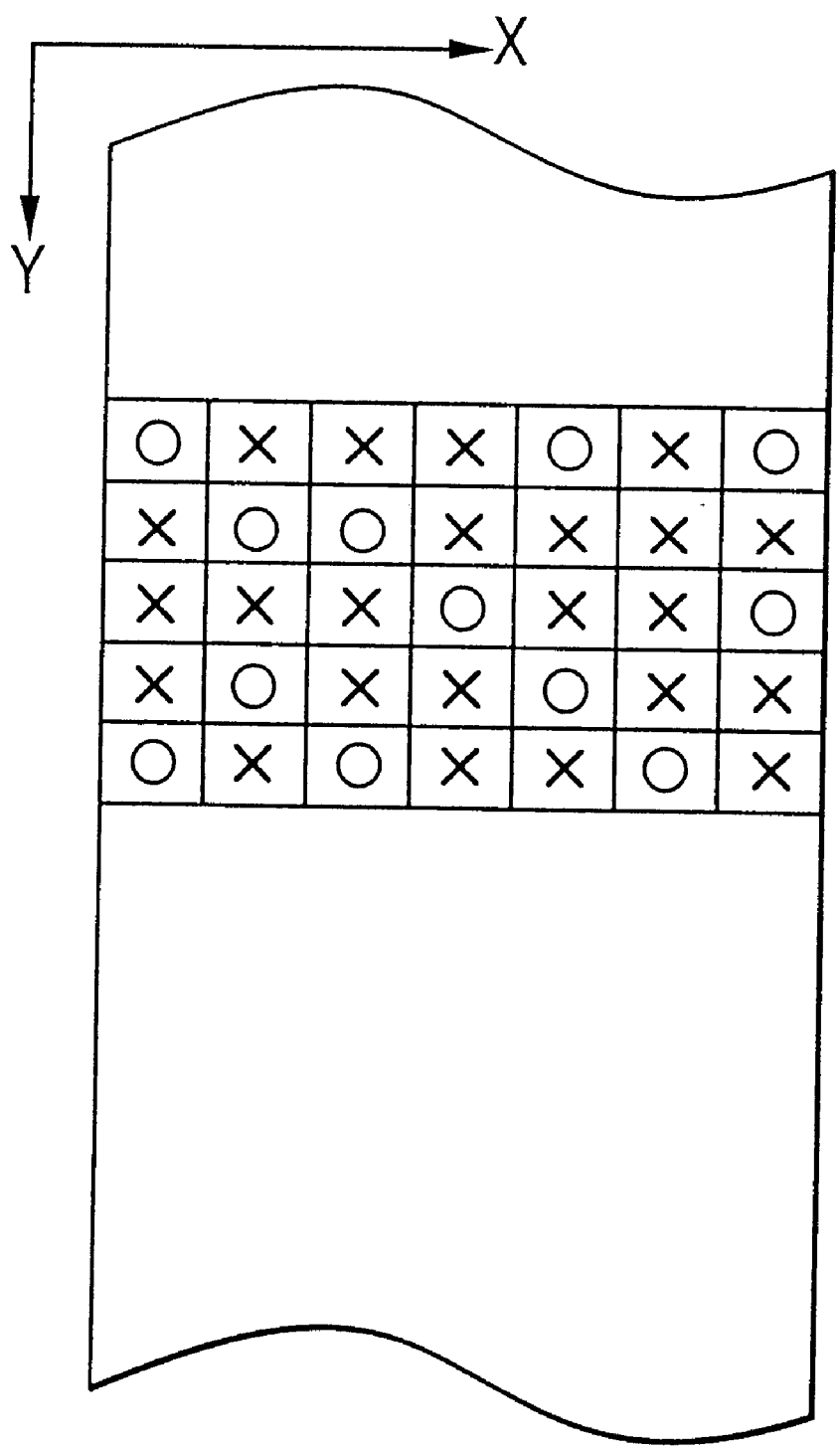
FIG. 10 is an explanatory view for illustrating a distortion correction process using an interpolation method.
Figure 13A:
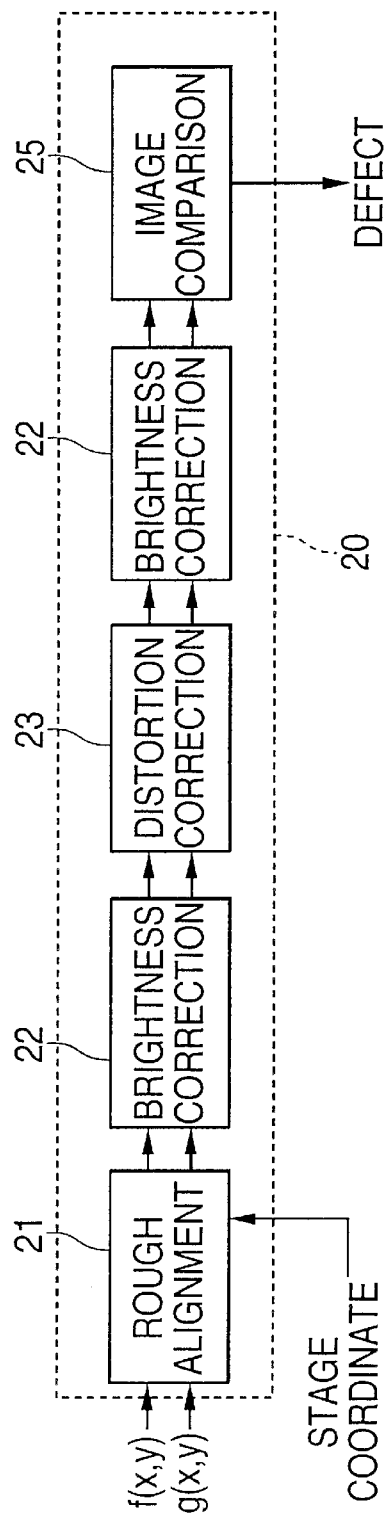
FIGS. 13a–d are further block diagrams showing further image processing and defect determination units according to the present invention.
Figure 13B:
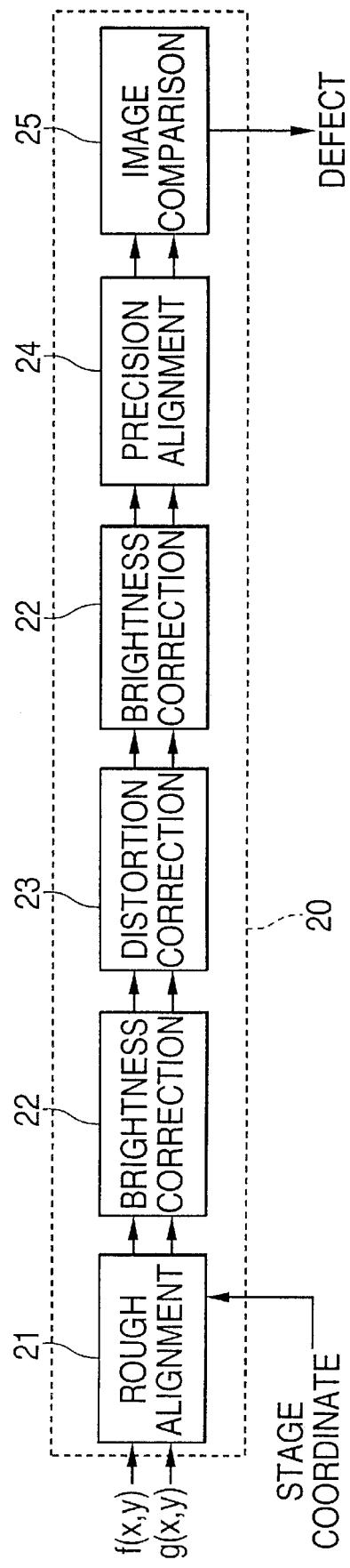
Figure 13C:
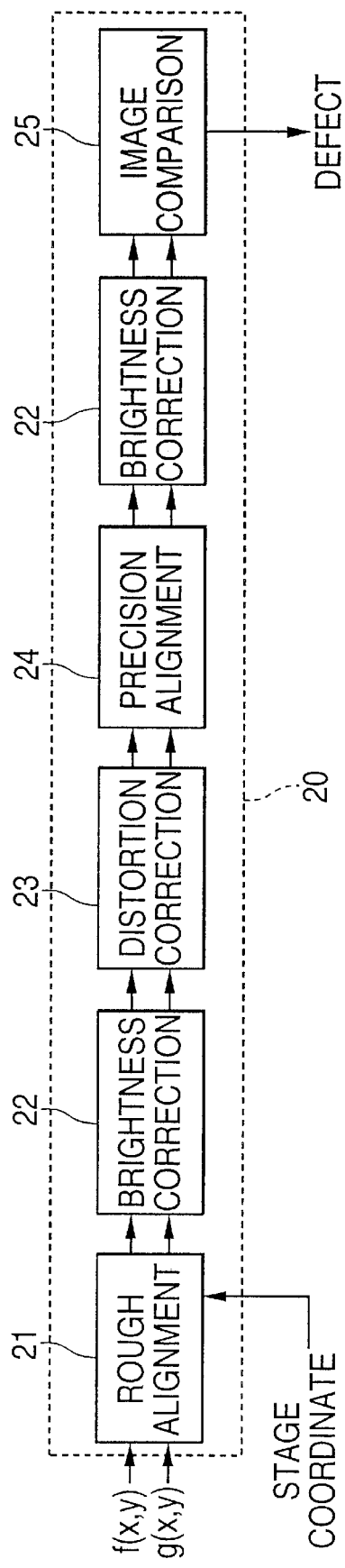
Figure 13D:
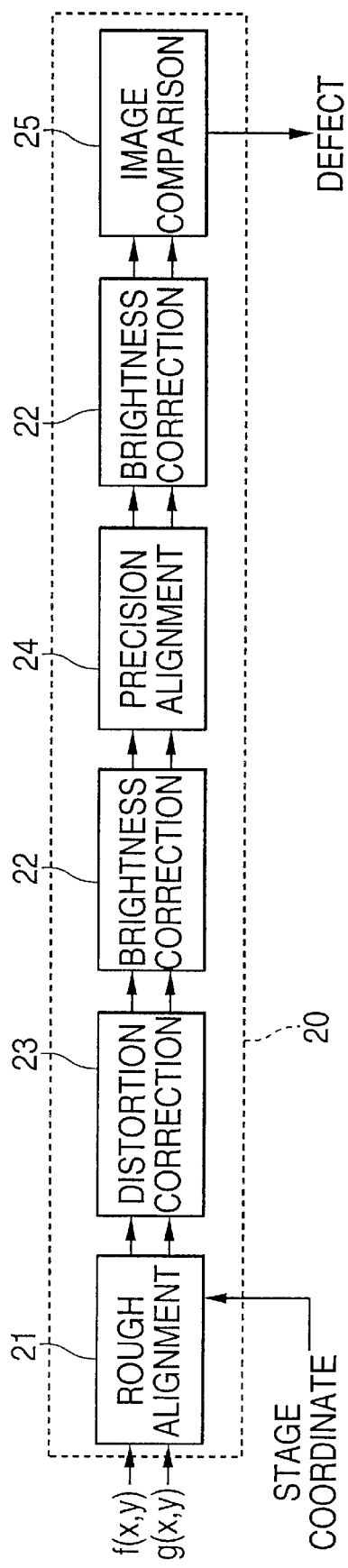

Next, a spatial distortion correction process using an interpolation method will be described. Previously, a stepwise alignment method was described to perform more accurate alignment. In practice, however, there may exist situations wherein some division units cannot themselves provide any alignment or misregistration information, for example, if a division unit pertains only to a background brightness and has no or unreliable alignment features therein, no alignment or misregistration information can be obtained therefrom. The present method described herein utilizes misregistration detection results from division units which are capable of providing alignment or misregistration information to then interpolate misregistration detection results for division units incapable of providing alignment or misregistration information. More specifically, in FIG. 10, an O symbol designates a division unit at which the amount of misregistration has been determined, and an X symbol designates a division unit in which the amount of misregistration cannot be determined. The amount of misregistration for one or more neighboring O division areas is then used to interpolate misregistration for a subject X division unit.

Whether or not the amount of misregistration can be determined to match is judged by whether or not a single possible shifted position (as opposed to multiple position candidates) can be determined to increase the degree of matching when, for example, a reference image is shifted one pixel at a time with respect to the inspected image to obtain the degree of matching. As a non-exhaustive listing of useable interpolation methods, any of a straight line (or plane) interpolation, spline curve (or curved surface) interpolation or the like can be used.

Next, the precision alignment process will be described. First, a relative amount of misregistration of both images not exceeding a pixel value is calculated. Thereafter, as a method of implementing precision alignment, there are at least two applicable methods, i.e., one is to relatively shift each image for laying one on top of the other, and the other is to correct the brightness value of each image on the basis of the amount of misregistration.

First, concrete description will be made of a method of calculating the relative amount of misregistration of both images not exceeding a pixel value. Assuming images aligned in units of pixels to be f1 and g1, the amount (i.e., real number in a range of 0 to 1) of misregistration not exceeding a pixel is calculated for these two images. As measure of degree of positional matching of the two images, such choices as shown in the following equations are conceivable.

$$\max|f0-g0|\Sigma\Sigma|f0-g0|, \Sigma\Sigma(f0-g0)^2 \qquad \text{(equation 4)}$$

An example in which "square sum of difference" described has been adopted. Assuming an amount of misregistration at a middle position between f1 and g1 to be zero, f1 deviates $-\delta x$ in the x direction and $-\delta y$ in the y direction and g1 deviates $+\delta x$ in the x direction and $+\delta y$ in the y direction. Namely, an amount of deviation between f1 and g1 is $2*\delta x$ in the x direction and $2*\delta y$ in the y direction. Since $\delta x$ and $\delta y$ are non-integers, it is necessary to define a value between pixels to deviate by $\delta x$ and $\delta y$. An image f2 obtained by deviating f1 by $\delta x$ in the x direction and by $\delta y$ in the y direction, and an image g2 obtained by deviating g1 by $-\delta x$ in the x direction and by $-\delta y$ in the y direction, are defined as follows:

$$f2(x, y)=f1(x+dx, y+dy)=f1(x, y)+dx*(f1(x+1, y)-f1(x, y))+dy*(f1(x, y+1)-f1(x, y)) \qquad \text{(equation 5)}$$

$$g2(x, y)=g1(x-dx, y-dy)=g1(x, y)+dx*(g1(x-1, y)-g1(x, y))+dy*(g1(x, y-1)-g1(x, y)) \qquad \text{(equation 6)}$$

Equations 5 and 6 are a so-called linear interpolation. The degree of matching $\epsilon 2[\delta x, \delta y]$ of f2 and g2 is defined by the "square sum of difference" as follows:

$$\epsilon 2(\delta x, \delta y)=\Sigma\Sigma(f2(x, y)-g2(x, y))^2 \qquad \text{(equation 7)}$$

The object of the precision alignment unit 22 is to determine a value $\delta x0$ for $\delta x$, and a value $\delta y0$ for $\delta y$, which cause $\epsilon 2[\delta x, \delta y]$ to take a minimum value. For that end, an equation obtained by partially differentiating equation 7 with respect to δx and δy is placed to be equal to zero, and it is solved with respect to δx and δy to determine δx0 and δy0.

The method for relatively shifting both images to lay one on top of the other for precision alignment is implemented by substituting δx0 and δy0 thus determined into equations 5 and 6 to shift each image to the position O in an amount equal to misregistration. The images f2 and g2 thus obtained are aligned at a precision not exceeding a pixel. This method is similar to the method used for an ordinary optical inspection apparatus.

Next, description will be made of a precision alignment method by correcting the brightness value of an image on the basis of the amount of misregistration. Since an amount of misregistration at the middle position between f1 and g1 is assumed to be zero, and f1 deviates −δx in the x direction and −δy in the y direction and g1 deviates +δx in the x direction and +δy in the y direction, the brightness of each image at the position of O in amount of misregistration is given by the following equations:

$$f3 = f1(x, y) + dx1(x, y)*\delta x + dy1(x, y)*\delta y \quad \text{(equation 8)}$$

$$g3 = g1(x, y) - dx2(x, y)*\delta x - dy2(x, y)*\delta y \quad \text{(equation 9)}$$

where $$dx1(x, y) = f1(x+1, y) - f1(x, y) \quad \text{(equation 10)}$$

$$dx2(x, y) = g1(x, y) - g1(x-1, y) \quad \text{(equation 11)}$$

$$dx1(x, y) = f1(x, y+1) - f1(x, y) \quad \text{(equation 12)}$$

$$dx2(x, y) = g1(x, y) - g1(x, y-1) \quad \text{(equation 13)}$$

since f3=g3

$$g1(x, y) = f1(x, y) + A(x, y) \quad \text{(equation 14)}$$

$$A(x, y) = (dx1(x, y) + dx2(x, y))*\delta x + (dy1(x, y) + dy2(x, y))*\delta y \quad \text{(equation 15)}$$

The precision alignment can be achieved by correcting the brightness value of f1 by A.

A[x, y] is a term for correcting the difference in brightness value between both images correspondingly to the amounts of misregistration δx0 and δy0 not exceeding a pixel value. Since dx1 represented by, for example, equation 10 is a local rate of change of the gradation value of f1 in the x direction, dx1(x, y)*δx0 can be said to be a predicted value for change in a gradation value of f1 when the position deviates by δx0. Accordingly, the first term of A(x, y) can be said to be a value obtained by predicting for each pixel how much the gradation value for a differential image between f1 and g1 varies when the position of f1 and the position of g 1 are deviated by δx0 and −δx0 in the x direction, respectively. Similarly, the second term can be said to be a value predicted in the y direction. The difference in brightness value between two images due to the known misregistration δx0 and δy0 can be canceled by A(x, y).

In the foregoing, the combination of processes shown in FIG. 2 was described, and in order to detect defects not less than a pixel, the precision alignment process may be omitted as shown in FIG. 11. Also, in order to correct the brightness effectively, patterns contained in two images are preferably the same. For an object whose correction of distortion functions effectively even if the brightness is not corrected, the brightness correction may be performed after the precision alignment if circumstances require after the distortion correction as shown in FIGS. 12a–c. If the distortion correction, and the brightness correction before the precision alignment are required, and the brightness correction is performed in the same pattern area again, it will be possible to realize the alignment process of two images at the position and in the direction of brightness more strictly. Embodiments of alternative combinations of processes for realizing the alignment and defect detection processes are shown in FIGS. 13a–d.

FIG. 14 shows another embodiment for the image processing and defect determination unit of a visual inspection apparatus according to the present invention. A limited amount of brightness correction 30 and the size of a brightness correction area 31 are arranged to be able to be inputted into the brightness correction circuit 22. In particular, this limited amount of brightness correction 30 and the size of the brightness correction area 31 are arranged to be able to be read from a memory medium such as a hard disk and a floppy disk as one of the inspection parameters before the commencement of the inspection. In this way, it is possible to set an optimum limited amount of correction suitable for the pattern in such a manner that the limited amount of correction is reduced for a pattern in which a defect that could be detected only by such brightness difference as residues at the bottoms of fine holes is very likely to occur, and that the limited amount of correction is increased for a pattern in which the difference in film thickness is prone to affect the brightness, or which is easily affected by charge-up or the like. Also, if the limited amount of correction is caused to be furnished from a menu on the operation screen, it will facilitate evaluating the performance by experimentally setting the limited amount of correction for a pattern to be inspected whose optimum limited amount of correction is unknown.

Also, in the embodiments described above, the description has been made of apparatuses using electronic optical detection means, but it is needless to say that the present invention can be applied to methods using any detection means such as optical detection means as shown in FIG. 15 in the same manner.

More specifically, FIG. 15 shows the schematic structure of a pattern inspection device using optical detection means (detection unit) 201. The detection unit 201 is composed of a stage 202 for moving in x and y directions with an object inspected 200 such as a semiconductor wafer placed thereon, a light source 203, an illumination optical system 204 for concentrating light emitted from the light source 203, an objective lens 205 for illuminating the illumination light concentrated by the illumination optical system 204 onto the object inspected 200 to form an optical image reflected from the object inspected 200, and a one-dimensional image sensor 206, which shows an embodiment of a photoelectric conversion element for receiving an optical image formed by a detection optical system including the objective lens 205 to convert it into an image signal in proportion to the brightness. Thus, an image signal detected by the one-dimensional image sensor 206 in the detection unit 201 is inputted into an image input unit 212. The image input unit 212 has a A/D converter 207, an image memory 210 for storing, when a digital image signal having a gradation value obtained from the A/D converter 207 is divided into two systems, the digital image signal for forming a comparison image f(x, y) and an image memory 211 for storing the digital image signal through a delay circuit 209 for forming a reference image g(x, y). Naturally, the image input unit 212 may be provided with a pre-treatment circuit 208 such as shading correction, dark level correction and filtering processes. The resultant f(x, y) and g(x, y) correspond to two each of input image data in FIGS. 2, 11, 12 and 13. An image processing unit 213 is composed of one of processing blocks shown in FIG. 2, FIG. 11, FIG. 12 or FIG. 13, and is capable of determining a defect based on the same image processing.

As described above, in an image detection process using electron beams, there is a problem that a brightness difference is caused in normal patterns between images to be compared under the influences of a difference in film thickness of such a degree that should be permitted as a normal portion or the charge-up, and this brightness difference is falsely recognized to be defective. Also, there is also a problem that eddy currents generated by the change in a relative speed of electron beams to the object inspected causes misregistration in the detected image under the influence of an electric field, this is detected as the distorted image, and it is difficult to perform alignment over the entire image in the image comparison according to the prior art, thus even the normal position being falsely recognized to be defective. According to the present invention, it is possible to reduce the probability of false detection by correcting the brightness difference to perform the alignment in accordance with the degree of the distortion. Also, by setting the limited amount for the brightness correction, it is possible to detect, without overlooking, a defect that could be detected only by a difference in brightness such as resist residues at the bottoms of fine holes while any brightness difference in the normal pattern portion is being permitted. Thus it is possible to realize a highly reliable inspection.

Figure 17:
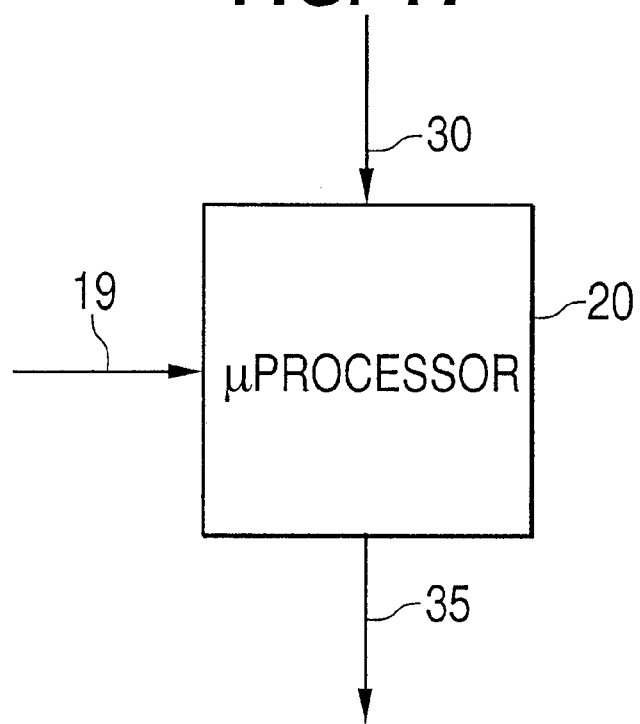
FIG. 17 is illustrative of an image processing and defect determination unit being provided in the form of a microprocessor.
Figure 18:
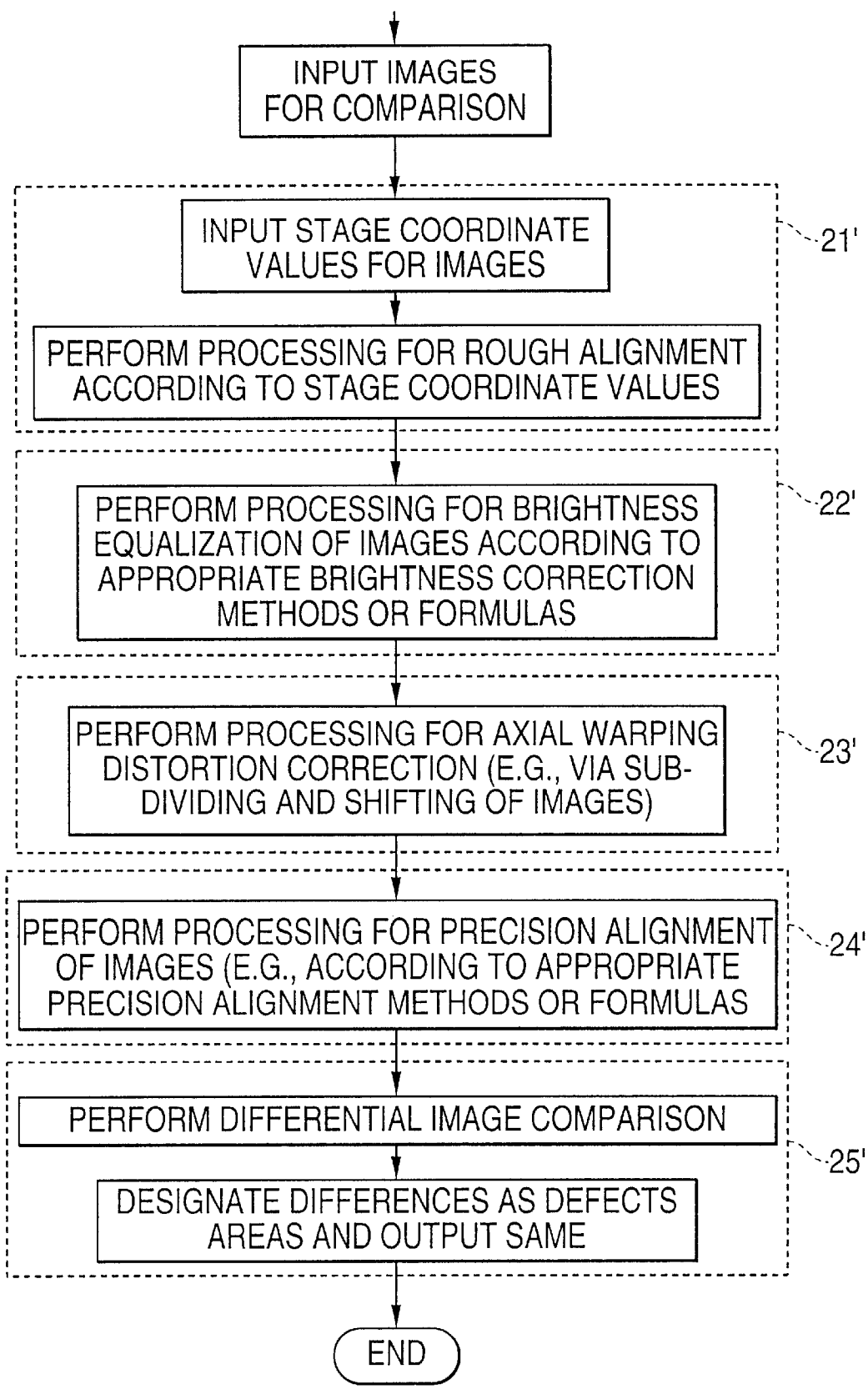
FIG. 18 is a flowchart of processings performed by the microprocessor of FIG. 17.

The image processing and defect determination unit 20 can be in the form of a microprocessor as shown in FIG. 17, wherein each of the rough alignment 21, brightness correction 22, distortion correction 23, precision alignment 24 and image comparison processes (discussed ahead) are performed via operation of the microprocessor via suitable programming to perform the flowchart steps illustrated in FIG. 18. As should be apparent from FIG. 16, the only flowchart steps necessary of a most simplistic embodiment of the present invention would be those for brightness level correction 22 and image comparison 25, i.e., one or more of the rough alignment 21, distortion correction 23 and precision alignment 24 flowchart steps can be omitted. Further, the rough alignment 21, brightness level correction 22, distortion correction 23 and precision alignment 24 flowchart steps can be freely rearranged with each other and/or duplicated, to obtain any of the alternative embodiments of FIGS. 11, 12a–c and 13a–d.

This concludes the description of the preferred embodiments.

Although the present invention has been described with reference to a number of illustrative embodiments thereof, it should be understood that numerous other modifications and embodiments can be devised by those skilled in the art that will fall within the spirit and scope of the principles of this invention. More particularly, reasonable variations and modifications are possible in the component parts and/or arrangements of the subject combination arrangement within the scope of the foregoing disclosure, the drawings and the appended claims without departing from the spirit of the invention, e.g., the following represents a non-exhaustive list of modifications which might readily be apparent to one skilled in the art to which the present invention is directed.

What is claimed is:

1. A pattern inspection method, comprising the steps of:
   obtaining from an object at least two images from at least two different areas having corresponding patterns formed thereon by a detector;
   correcting a brightness level of each of a plurality of corresponding areas of said at least two images so that a brightness level of said each of a plurality of corresponding areas of said at least two images substantially coincide with each other;
   correcting distortion of at least one of said images of said patterns formed on said object; and
   detecting a defect as a portion of said images which are different from each other by comparing images after said correcting brightness level step and said correcting distortion level step.

2. A pattern inspection method as claimed in claim 1, wherein said correcting brightness levels step is correcting a distribution of brightness level of the image so as to substantially coincide with that of the other image to be compared.

3. A pattern inspection method as claimed in claim 1, wherein in the step of said correcting distortion, said each of a plurality of corresponding areas of said at least two images are made to align.

4. A pattern inspection method, comprising the steps of:
   scanning an electron beam on a surface of an object on which plural patterns are formed;
   detecting by a detector an electron emanated from the surface of the object by scanning the electron beam;
   obtaining from the detected electron by said detector at least two images of at least two different areas having corresponding patterns which are formed on the object;
   correcting brightness levels of at least one of said images obtained through said detector to make brightness levels of said at least two images more closely coincide in brightness level with each other;
   correcting distortion of at least one of said images of said patterns; and
   detecting a defect as a portion of said images which are different from each other by comparing images and distinguishing said patterns after said correcting brightness levels step and said correcting distortion step.

5. A pattern inspection method as claimed in claim 4, said correcting distortion comprising:
   rough aligning said images based upon coordinate information provided with each image to match coordinate positions of said images with one another;
   correcting axial warping distortions existing between said images to substantially match plane coordinates for said images; and
   precision aligning said images by performing alignment not exceeding a pixel distance.

6. A pattern inspection method as claimed in claim 5, wherein said step of correcting axial warping distortion is performed, and wherein said correcting brightness levels step is performed before said step of correcting axial warping distortion.

7. A pattern inspection method as claimed in claim 5, wherein said rough aligning, said correcting axial warping distortion, said correcting brightness levels, said precision aligning and said detecting steps are all performed, and in a stated order.

8. A pattern inspection method as claimed in claim 5, wherein said correcting step is performed, and wherein said correcting step is performed before said correcting brightness levels step.

9. A pattern inspection method as claimed in claim 5, wherein said rough aligning, said correcting, said precision aligning, said correcting brightness levels and said detecting steps are all performed, and in a stated order.

10. A pattern inspection method as claimed in claim 5, wherein said rough aligning step, said correcting brightness levels step performed a second time, and said detecting step are all performed, and in a stated order.

11. A pattern inspection method as claimed in claim 5, wherein said rough aligning step, said correcting brightness levels step performed a first time, said correcting step, said correcting brightness levels step performed a second time, said precision aligning step, and said detecting steps are all performed, and in a stated order.

12. A pattern inspection method as claimed in claim 5, wherein said rough aligning step, said correcting brightness levels step performed a first time, said correcting step, said precision aligning step, said correcting brightness levels step performed a second time, and said detecting step are all performed, and in a stated order.

13. A pattern inspection method as claimed in claim 5, wherein said rough aligning step, said correcting step, said correcting brightness levels step performed a first time, said precision aligning step, said correcting brightness levels step performed a second time, and said detecting step are all performed, and in a stated order.

14. A pattern inspection method as claimed in claim 5, wherein at least one of said rough aligning step, correcting step, said correcting brightness levels step, said precision aligning step, and said detecting step is performed using a programmed microprocessor.

15. A pattern inspection method as claimed in claim 5, wherein said correcting brightness levels step is performed twice.

16. A visual inspection method as defined in claim 4, wherein said images are divided into areas of predetermined size, and said correcting brightness levels step is performed for each area.

17. A pattern inspection method as claimed in claim 4, wherein said obtaining step more specifically comprises using a scanning electron microscope (SEM) to obtain said images.

18. A pattern inspection method as claimed in claim 17, wherein said correcting brightness levels step is more specifically for removing brightness level distortions resultant at least in part from charge build-up in said at least one object from electron scanning using said SEM.

19. A pattern inspection method as claimed in claim 4, wherein said obtaining step more specifically comprises using an optical inspection apparatus to obtain said images.

20. A pattern inspection method as claimed in claim 19, wherein said obtaining step more specifically uses said optical inspection apparatus to obtain images of at least one semiconductor substrate, and said equalizing step is more specifically for removing brightness level distortions resultant at least in part from observing through varying layer thicknesses of said at least one semiconductor substrate.

21. A pattern inspection method as claimed in claim 4, wherein a limit value for an amount of correcting brightness levels is furnished in advance, and said correcting brightness levels step is performed not to exceed said limit value.

22. A pattern inspection method as claimed in claim 4, wherein said limit value is read from a memory medium such as a hard disk or a floppy disk or is furnished from a user's real-time entry as one of inspection parameters before commencement of said correcting brightness levels step.

23. A pattern inspection method as claimed in claim 4, wherein a brightness value of one image is linearly transformed, and said correcting brightness levels step is performed by determining a coefficient of linear transformation so that a sum of a square of a difference between said image and another image for each pixel is minimized.

24. A pattern inspection method as claimed in claim 4, wherein a plurality of peak positions are calculated from a histogram for a brightness value of one image, and said correcting brightness levels step is performed by changing the brightness value of said one image so that said peak positions coincide with peak positions in a histogram for a brightness value of another image calculated in a same manner.

25. A pattern inspection method as claimed in claim 4, wherein said correcting brightness levels step is performed by changing a brightness value of one image so that a histogram for the brightness value of said one image coincides in shape with a histogram for a brightness value of another image.

26. A pattern inspection method as claimed in claim 4, wherein said correcting brightness levels step is performed by changing brightness values of said images so that histograms for the brightness values of said images coincide in shape with a predetermined histogram provided in advance.

27. A pattern inspection apparatus, comprising:
   an imager obtaining, from at least one object on which a plurality of patterns are formed, at least two images from at least two different areas having corresponding patterns, by scanning an electron beam on a surface of an object and detecting by a detector an electron emanated from a surface of the object by scanning the electron beam;
   a brightness corrector correcting a brightness level of each of a plurality of corresponding areas of said at least two images so that a brightness level of said each of a plurality of corresponding areas of said at least two images substantially coincide with each other;
   a distortion corrector correcting distortion of at least one of said images of said pattern; and
   a defect detector detecting a defect as a portion of said images which are different from each other by comparing images and distinguishing from said pattern after treatment by said brightness corrector and said distortion corrector.

28. A pattern inspection apparatus as claimed in claim 27, said distortion corrector comprising:
   a rough aligner roughly aligning said images based upon coordinate information provided with each image to match coordinate positions of said images with one another;
   a spatial corrector correcting axial warping distortions existing between said images to substantially match plane coordinates for said images; and
   a precision aligner precision aligning said images by performing alignment not exceeding a pixel distance.

29. A pattern inspection apparatus as claimed in claim 28, wherein said spatial corrector is included, and wherein said brightness corrector performs before said spatial corrector.

30. A pattern inspection apparatus as claimed in claim 28, wherein said rough aligner, said spatial corrector, said brightness corrector, said precision aligner and said defect detector are all included, and perform in a stated order.

31. A pattern inspection apparatus as claimed in claim 28, wherein said spatial corrector is included, and wherein said spatial corrector performs before said brightness corrector.

32. A pattern inspection apparatus as claimed in claim 28, wherein said rough aligner, said spatial corrector, said precision aligner, said brightness corrector and said defect detector are all included, and perform in a stated order.

33. A pattern inspection apparatus as claimed in claim 28, wherein said rough aligner, a first said brightness corrector, said spatial corrector, a second said brightness corrector, and said defect detector are all included, and perform in a stated order.

34. A pattern inspection apparatus as claimed in claim 28, wherein said rough aligner, a first said brightness corrector, said spatial corrector, a second said brightness corrector, said precision aligner, and said defect detector are all included, and perform in a stated order.

35. A pattern inspection apparatus as claimed in claim 28, wherein said rough aligner, a first said brightness corrector, said spatial corrector, said precision aligner, a second said brightness corrector, and said defect detector are all included, and perform in a stated order.

36. A pattern inspection apparatus as claimed in claim 28, wherein said rough aligner, said spatial corrector, a first said brightness corrector, said precision aligner, a second said brightness corrector, and said defect detector are all included, and perform in a stated order.

37. A pattern inspection apparatus as claimed in claim 28, wherein at least one of said rough aligner, said spatial corrector, said brightness corrector, said precision aligner, and said defect detector is performed using a programmed microprocessor.

38. A pattern inspection apparatus as claimed in claim 28, wherein said brightness corrector performs twice.

39. A visual inspection apparatus as defined in claim 27, wherein said images are divided into areas of predetermined size, and said brightness corrector operation is performed for each area.

40. A pattern inspection apparatus as claimed in claim 27, wherein said imager is more specifically a scanning electron microscope (SEM).

41. A pattern inspection apparatus as claimed in claim 40, wherein said brightness corrector operation is more specifically for removing brightness level distortions resultant at least in part from charge build-up in said at least one object from electron scanning using said SEM.

42. A pattern inspection apparatus as claimed in claim 27, wherein said imager is more specifically an optical inspection apparatus.

43. A pattern inspection apparatus as claimed in claim 42, wherein said imager more specifically uses said optical inspection apparatus to obtain images of at least one semiconductor substrate, and said brightness corrector operation is more specifically for removing brightness level distortions resultant at least in part from observing through varying layer thicknesses of said at least one semiconductor substrate.

44. A pattern inspection apparatus as claimed in claim 27, wherein a limit value for an amount of brightness correction is furnished in advance, and said brightness correction is performed not to exceed said limit value.

45. A pattern inspection apparatus as claimed in claim 27, wherein said limit value is read from a memory medium such as a hard disk or a floppy disk or is furnished from a user's real-time entry as one of inspection parameters obtain before commencement of said brightness correction.

46. A pattern inspection apparatus as claimed in claim 27, wherein a brightness value of one image is linearly transformed, and said brightness corrector operation is performed by determining a coefficient of linear transformation so that a sum of a square of a difference between said image and another image for each pixel is minimized.

47. A pattern inspection apparatus as claimed in claim 27, wherein a plurality of peak positions are calculated from a histogram for a brightness value of one image, and said brightness corrector operation is performed by changing the brightness value of said one image so that said peak positions coincide with peak positions in a histogram for a brightness value of another image calculated in a same manner.

48. A pattern inspection apparatus as claimed in claim 27, wherein said brightness corrector operation is performed by changing a brightness value of one image so that a histogram for the brightness value of said one image coincides in shape with a histogram for a brightness value of another image.

49. A pattern inspection apparatus as claimed in claim 27, wherein said brightness corrector operation is performed by changing brightness values of said images so that histograms for the brightness values of said images coincide in shape with a predetermined histogram provided in advance.

50. A pattern inspection apparatus as claimed in claim 27, wherein said distortion corrector corrects distortion of at least one of said images of said pattern by aligning said each of a plurality of corresponding areas of said at least two images.

51. A pattern inspection method, comprising the steps of:
    obtaining from an object at least two images from at least two different areas having corresponding patterns formed thereon by a detector;
    correcting brightness levels of at least one of said images of said patterns formed on said object and obtained by said detector to be closer to a brightness level of another one of said at least two images to make brightness levels of said at least two images more closely coincide in brightness level with each other;
    correcting distortion of at least one of said images of said patterns formed on said object; and
    detecting a defect as a portion of said images which are different from each other by comparing images after said correcting brightness level step and said correcting distortion step.

52. A pattern inspection method as claimed in claim 51, wherein said correcting brightness levels corrects brightness levels of said at least one of said images to substantially said brightness level of said another one of said at least two images.

53. A pattern inspection method as claimed in claim 51, wherein said correcting distortion corrects geometrical distortion to make geometries of patterns within said at least two images more closely coincide with each other.

54. A pattern inspection method, comprising the steps of:
    scanning an electron beam on a surface of an object on which plural patterns are formed;
    detecting by a detector an electron emanated from the surface of the object by scanning the electron beam;
    obtaining from the detected electron by said detector at least two images of at least two different areas having corresponding patterns which are formed on the object;
    correcting brightness levels of at least one of said images obtained through said detector, to be closer to a brightness level of another one of said at least two images to make brightness levels of said at least two images more closely coincide in brightness level with each other;
    correcting distortion of at least one of said images of said patterns; and
    detecting a defect as a portion of said images which are different from each other by comparing images and distinguishing said patterns after said correcting brightness levels step and said correcting distortion step.

55. A pattern inspection method as claimed in claim 54, wherein said correcting brightness levels corrects brightness levels of said at least one of said images to substantially said brightness level of said another one of said at least two images.

56. A pattern inspection method as claimed in claim 54, wherein said correcting distortion corrects geometrical distortion to make geometries of patterns within said at least two images more closely coincide with each other.

57. A pattern inspection apparatus, comprising:

an imager obtaining, from at least one object on which a plurality of patterns are formed, at least two images from at least two different areas having corresponding patterns, by scanning an electron beam on a surface of an object and detecting by a detector an electron emanated from a surface of the object by scanning the electron beam;

a brightness corrector correcting brightness levels of at least one of said images obtained through said detector, to be closer to a brightness level of another one of said at least two images to make brightness levels of said at least two images more closely coincide in brightness level with each other;

a distortion corrector correcting distortion of at least one of said images of said pattern; and a defect detector detecting a defect as a portion of said images which are different from each other by comparing images and distinguishing from said pattern after treatment by said brightness corrector and said distortion corrector.

58. A pattern inspection apparatus as claimed in claim 57, wherein said correcting brightness levels corrects brightness levels of said at least one of said images to substantially said brightness level of said another one of said at least two images.

59. A pattern inspection apparatus as claimed in claim 57, wherein said correcting distortion corrects geometrical distortion to make geometries of patterns within said at least two images more closely coincide with each other.

* * * * *